United States Patent [19]

Nakai et al.

[11] Patent Number: 4,898,818
[45] Date of Patent: Feb. 6, 1990

[54] ANTITUMOR ACTIVE SUBSTANCE, PROCESS FOR PREPARING THE SAME, DRUG CONTAINING THE SUBSTANCE, GENE CODING FOR THE SUBSTANCE, VECTOR CONTAINING THE GENE AND RECOMBINANT MICROORGANISM

[75] Inventors: Satoru Nakai; Mayumi Kaneta; Yoshikazu Kikumoto, all of Tokushima; Yeong-Man Hong; Kazuyoshi Kawai, both of Naruto; Setsuko Takegata, Tokushima; Kiyoshi Ishii, Tokushima; Yasuo Yanagihara, Tokushima; Yoshikatsu Hirai, Tokushima, all of Japan

[73] Assignee: Otsuka Pharmaceutical Co., Ltd., Tokyo, Japan

[21] Appl. No.: 810,776

[22] Filed: Dec. 19, 1985

[30] Foreign Application Priority Data

| Dec. 21, 1984 | [JP] | Japan | 59-271207 |
| Jun. 24, 1985 | [JP] | Japan | 60-138280 |
| Jun. 24, 1985 | [JP] | Japan | 60-138281 |
| Oct. 3, 1985 | [JP] | Japan | 60-220882 |

[51] Int. Cl.$^4$ .................... C12P 21/00; C12N 15/00; C07K 13/00
[52] U.S. Cl. ................... 435/69.1; 435/172.3; 435/70.4; 435/69.5; 424/85.2; 530/351
[58] Field of Search ............. 435/68, 172.3, 70; 530/351

[56] References Cited

U.S. PATENT DOCUMENTS

| 4,762,914 | 8/1988 | Auron et al. ................ 435/68 |
| 4,766,069 | 8/1988 | Auron et al. ................ 435/68 |

FOREIGN PATENT DOCUMENTS

| 8652451 | 7/1986 | Australia . |
| 0109748 | 5/1984 | European Pat. Off. . |
| 0155433 | 9/1985 | European Pat. Off. . |
| 0161901 | 11/1985 | European Pat. Off. . |
| 0165654 | 12/1985 | European Pat. Off. . |
| 0188864 | 7/1986 | European Pat. Off. . |
| 0188920 | 7/1986 | European Pat. Off. . |
| 0200986 | 11/1986 | European Pat. Off. . |
| 60-149386 | 8/1985 | Japan . |
| WO8500830 | 2/1985 | PCT Int'l Appl. . |
| WO8504421 | 10/1985 | PCT Int'l Appl. . |

OTHER PUBLICATIONS

J. of Immunol., vol. 122, pp. 2112–2118 (1979).
Fed. Proc., vol. 41, pp. 257–262 (1982).
Cell. Immun., vol. 80, pp. 223–229 (1983).
Nature, vol. 309, pp. 56–59 (1984).
J. Exp. Med., vol. 160, pp. 772–787 (1984).
Cell. Immun., vol. 48, pp. 433–436 (1979).

(List continued on next page.)

*Primary Examiner*—Blondel Hazel
*Attorney, Agent, or Firm*—Sughrue, Mion, Zinn, Macpeak & Seas

[57] ABSTRACT

This invention provides an antitumor active substance GIF, a process for preparing the same, an antitumor composition containing the substance, a gene coding for GIF, a vector containing the gene and a recombinant microorganism, the substance GIF comprises as its component protein polypeptide A of the following primary structure.

```
Z Ala Pro Val Arg Ser Leu Asn Cys Thr Leu Arg
  Asp Ser Gln Gln Lys Ser Leu Val Met Ser Gly
  Pro Tyr Glu Leu Lys Ala Leu His Leu Gln Gly
  Gln Asp Met Glu Gln Gln Val Val Phe Ser Met
  Ser Phe Val Gln Gly Glu Glu Ser Asn Asp Lys
  Ile Pro Val Ala Leu Gly Leu Lys Glu Lys Asn
  Leu Tyr Leu Ser X   Val Leu Lys Asp Asp Lys
  Pro Thr Leu Gln Leu Glu Ser Val Asp Pro Lys
  Asn Tyr Pro Lys Lys Lys Met Glu Lys Arg Phe
  Val Phe Asn Lys Ile Glu Ile Asn Asn Lys Leu
  Glu Phe Glu Ser Ala Gln Phe Pro Asn Trp Tyr
  Ile Ser Thr Ser Gln Ala Glu Asn Met Pro Val
  Phe Leu Gly Gly Thr Lys Gly Gly Gln Asp Ile
  Thr Asp Phe Thr Met Gln Phe Val Ser Ser OH
``` wherein X is Cys or Ser and Z is H or a peptide represented by the amino acid sequence
or a peptide having the above sequence wherein at least one amino acid is removed from the N terminal or an amino acid.

2 Claims, 20 Drawing Sheets

OTHER PUBLICATIONS

Biochem. & Biophys. Res. Com., vol. 141, pp. 285–291 (1986).
J. Exp. Med., vol. 161, pp. 490–502 (1985).
J. Exp. Med., vol. 162, pp. 790–801 (1985).
J. Exp. Med., vol. 164, pp. 237–250 (1985).
The J. of Immunol., vol. 135, pp. 3962–3968 (1985).
The J. of Immunol., vol. 136, pp. 2483–2485 (1986).
Cell. Immun., vol. 63, pp. 164–176 (1981).
J. Exp. Med., vol. 150, pp. 709–714 (1979).
The J. of Immunol., vol. 130, pp. 2708–2714 (1983).
The J. of Immunol., vol. 132, pp. 1311–1316 (1984).
Nature, vol. 314, pp. 266–268 (1985).
Nature, vol. 312, pp. 458–462 (1984).
R. of Inf. Diseases, vol. 6, pp. 51–95 (1984).
The N.E. J. of Med., vol. 311, p. 1413 (1984).
Proc. Natl. Acad. Sci. USA, vol. 81, pp. 7907–7911 (1984).
Nature, vol. 315, pp. 641–647 (1985).
Nucleic Acids Res., vol. 13, pp. 5869–5882 (1985).
Nature, vol. 304, pp. 449–451 (1983).
The J. of Immunol., vol. 136, pp. 3098–3102 (1986).
J. Clin. Inv., vol. 79, pp. 48–51 (1987).
6th Intl. Cong. of Immun., pp. 343–346 (1986).
Biochem. & Biophys. Res. Comm., vol. 143, pp. 345–352 (1987).
Eur. J. Immunol., vol. 14, pp. 898–901 (1984).
Bio/Tech, vol. 4, pp. 1078–1082 (1986).
Clin. Exp. Immunol, vol. 55, pp. 295–302 (1984).
Arth. & Rheum., vol. 26, pp. 975–983 (1983).
Arth. & Rheum., vol. 28, pp. 853–862 (1985).
Immunol. Rev., vol. 63, pp. 51–72 (1982).
The J. of Immunol., vol. 136, pp. 2492–2497 (1986).
The J. of Immunol., vol. 136, pp. 3304–3310 (1986).
Immunol. Today, vol. 7, pp. 45–456 (1986).
Jpn. J. Cancer Res. (Gann), vol. 77, pp. 767–773 (1986).
Proc. of AARC, vol. 26, pp. 1058 (1985).
The Physiol., . . . Inteluekin-1, Liss, Alan R., pp. 253–262 (1985).

ANTITUMOR ACTIVE SUBSTANCE, PROCESS FOR PREPARING THE SAME, DRUG CONTAINING THE SUBSTANCE, GENE CODING FOR THE SUBSTANCE, VECTOR CONTAINING THE GENE AND RECOMBINANT MICROORGANISM

The present invention relates to an antitumor substance, and more particularly to a substance having activity to specifically inhibiting the growth of tumor cells, a process for preparing the substance, an antitumor composition containing the substance and a gene coding for the substance.

It is known that there are substances in the living body which act directly on tumor cells, exhibiting activity to selectively inhibit growth of such cell and eliminate them from the living body. These antitumor active substances so far reported include, for example, interferon (IFN), lymphotoxin (LT), tumor necrotizing factor (TNF), etc. (Evans, C. H., Cancer Immunol. Immunoether, 12, 181(1982)). Such antitumor active substances, which have activity to inhibit the growth of tumor cells, are thought to be useful as antitumor agents, while the structures of the genes corresponding to them are being clarified. Extensive research is being conducted on the production of these substances by genetic engineering techniques (Nature, Vol. 312, 20/27, p. 721 (1984); the same, Vol. 312, 20/27, p. 724 (1984), etc.)

An object of the present invention is to provide a novel antitumor active substance which differs from the above antitumor active substances reported in properties, characteristics, etc.

Another object of the invention is to provide a technique for preparing the novel antitumor active substance from immunologically competent cells derived from mammals.

Another objects of the invention is to provide a technique for preparing the antitumor active substance by a genetic engineering procedure.

Another object of the invention is to provide an antitumor composition comprising the antitumor active substance.

Another object of the invention is to provide a gene for preparing the antitumor active substance by the genetic engineering procedure, an expression vector having the gene incorporated therein, and a recombinant microorganisms incorporating the vector.

The above objects and other features of the invention will become apparent from the following detailed description.

The antitumor active substance of the present invention (hereinafter referred to as "GIF") has activity to inhibit growth of tumor cells (hereinafter referred to as "GIF activity") as determined by the method described later and is characterized in that it contains as its component protein, polypeptide A. Primary structure thereof is represented by the following formula (1).

Polypeptide A

Z Ala Pro Val Arg Ser Leu Asn Cys Thr Leu Arg
Asp Ser Gln Gln Lys Ser Leu Val Met Ser Gly
Pro Tyr Glu Leu Lys Ala Leu His Leu Gln Gly
Gln Asp Met Glu Gln Gln Val Val Phe Ser Met
Ser Phe Val Gln Gly Glu Glu Ser Asn Asp Lys
Ile Pro Val Ala Leu Gly Leu Lys Glu Lys Asn
Leu Tyr Leu Ser X Val Leu Lys Asp Asp Lys
Pro Thr Leu Gln Leu Glu Ser Val Asp Pro Lys
Asn Tyr Pro Lys Lys Lys Met Glu Lys Arg Phe
Val Phe Asn Lys Ile Glu Ile Asn Asn Lys Leu
Glu Phe Glu Ser Ala Gln Phe Pro Asn Trp Tyr
Ile Ser Thr Ser Gln Ala Glu Asn Met Pro Val
Phe Leu Gly Gly Thr Lys Gly Gly Gln Asp Ile
Thr Asp Phe Thr Met Gln Phe Val Ser Ser OH wherein X is Cys or Ser and Z is H or a peptide represented by the amino acid sequence Met Lys Cys Ser Phe Gln Asp Leu Asp Leu Cys
Pro Leu Asp Gly Gly Ile Gln Leu Arg Ile Ser
Asp His His Tyr Ser Lys Gly Phe Arg Gln Ala
Ala Ser Val Val Val Ala Met Asp Lys Leu Arg
Lys Met Leu Val Pro Cys Pro Gln Thr Phe Gln
Glu Asp Asp Leu Ser Thr Phe Phe Pro Phe Ile
Phe Glu Glu Glu Pro Ile Phe Phe Asp Thr Trp
Asp Asn Glu Ala Tyr Val His Asp or a peptide having the above sequence wherein at least one amino acid is removed from the N-terminal or an amino acid (Asp).

Briefly, the accompanying drawings describe the invention in further detail as follows.

Figure 15:
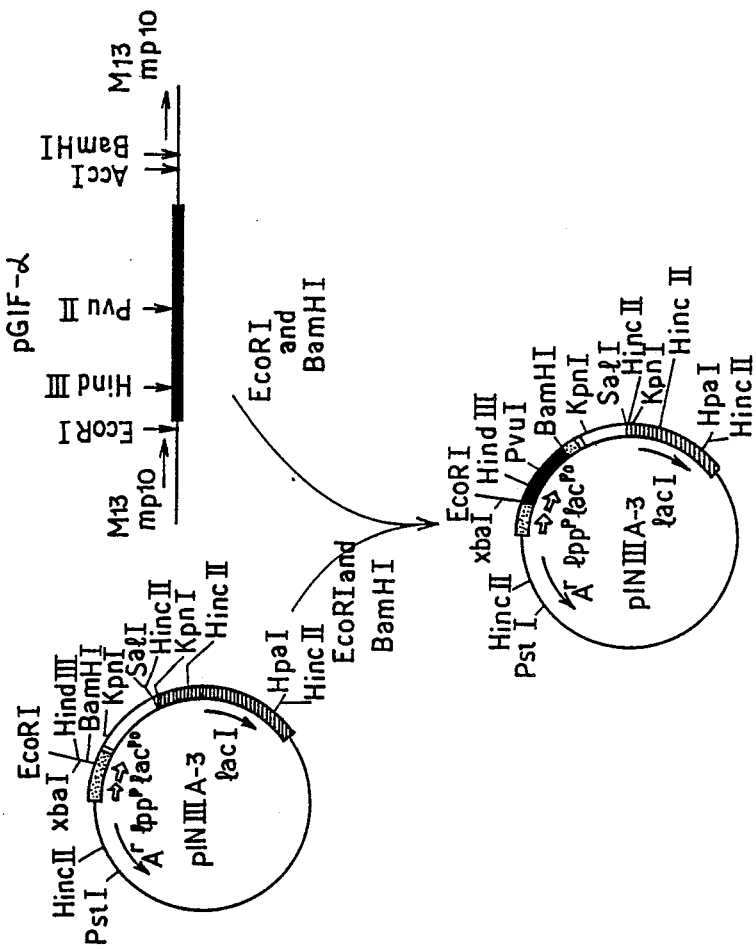
Figure 16:
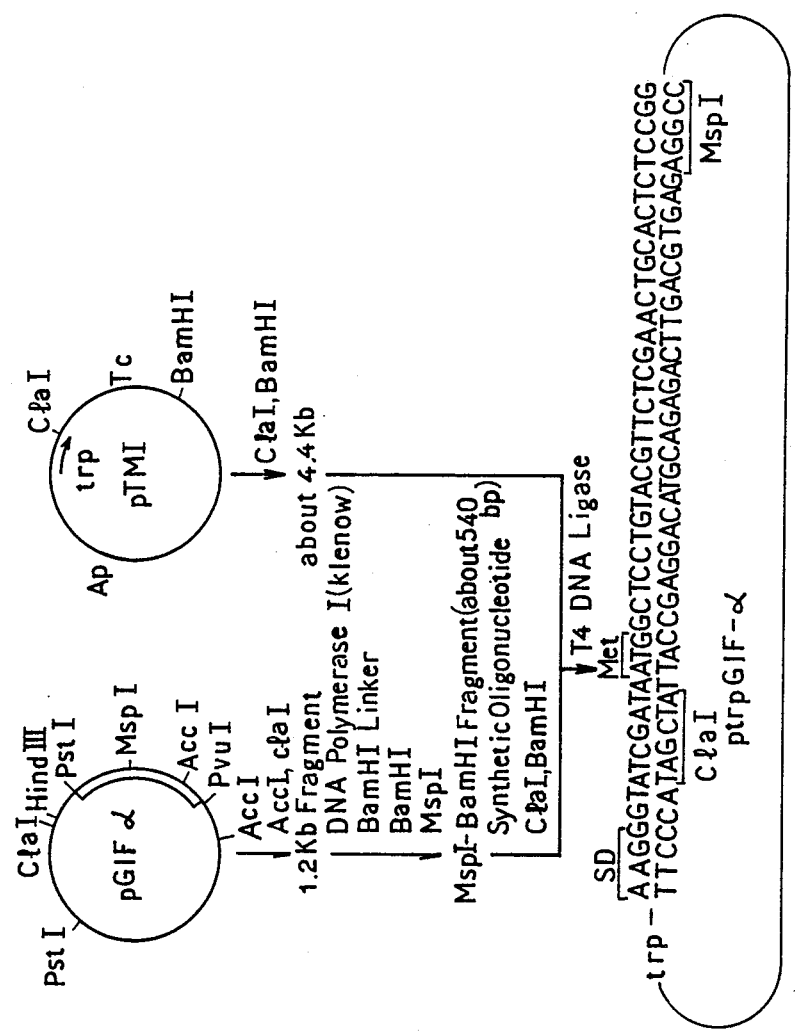
Figure 17:
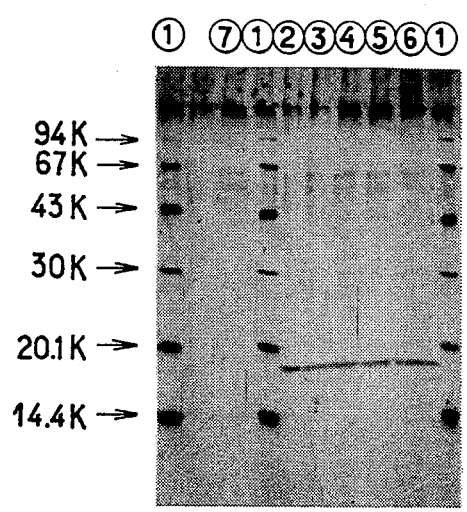
Figure 18:
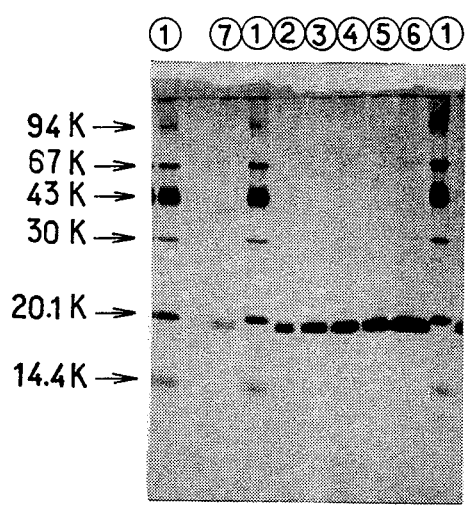
Figure 19:
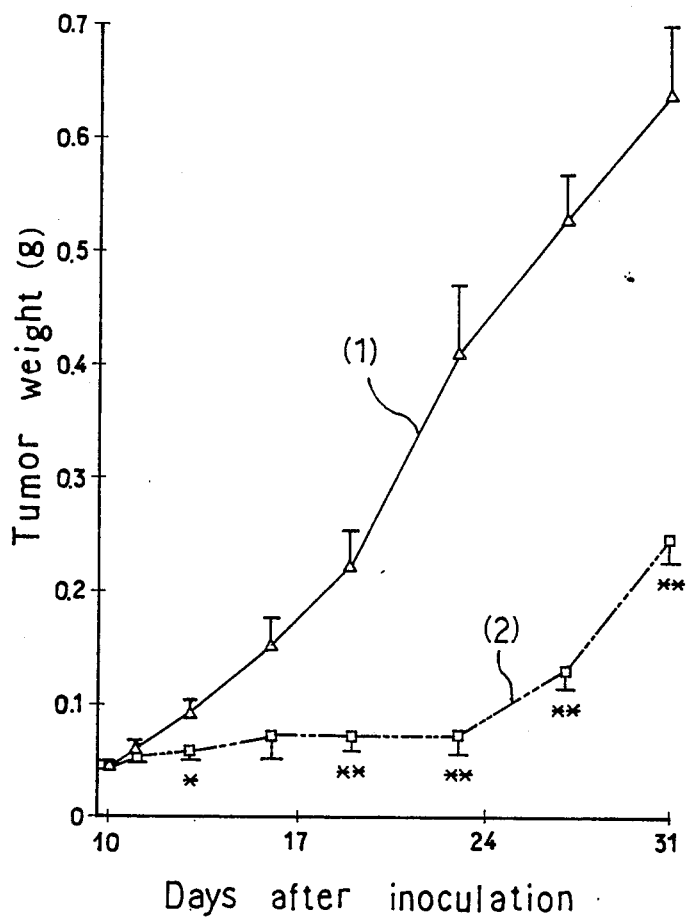
Figure 20:
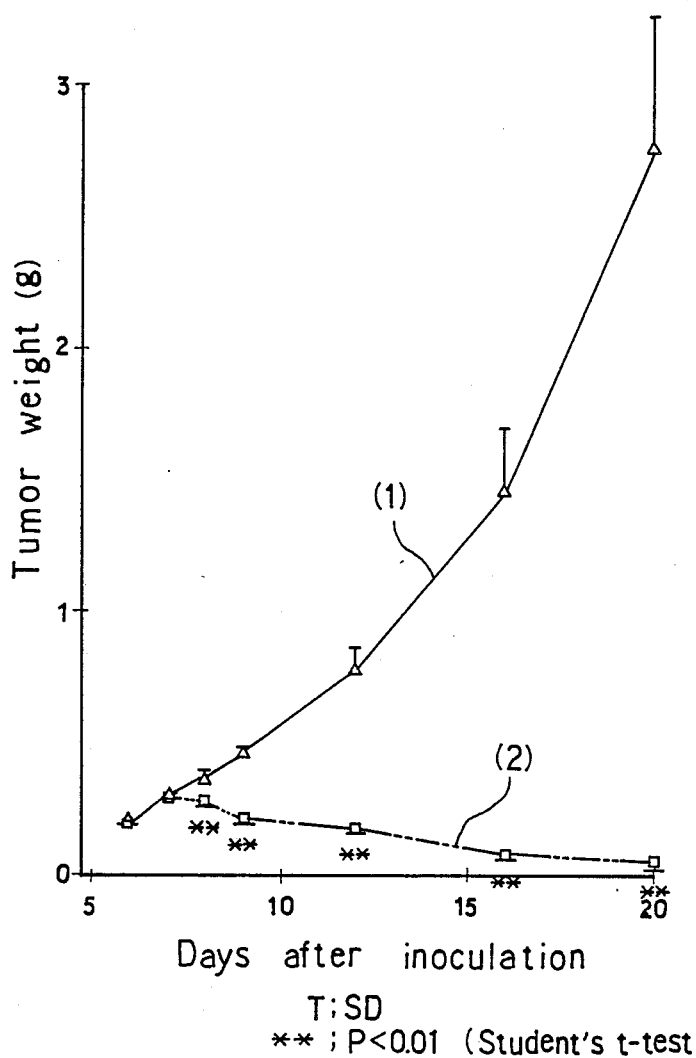

FIG. 15 schematically shows the protocol for production of plasmid pINIIf-GIF-α;

FIG. 16 shows the protocol for production of plasmid ptrpGIF-α;

FIG. 17 and FIG. 18 show electrophoresis gel results;

FIG. 19 shows test results on mouse inoculations with r-GIF in comparison with a control group and FIG. 20 shows similar results.

The peptides and amino acids are herein represented by symbols according to the nomenclature of amino acids adopted by IUPAC or by symbols representing amino acid residues and generally used in the art. The nucleic acids in the base sequence are also similarly represented.

With GIF of the present invention, the primary structure of the protein thereof is basically polypeptide I (of the formula (1) wherein X is Cys and Z is H) given below and having 153 amino acids in sequence, while the primary structure of the protein may have at the N-terminal of polypeptide I a desired peptide selected from 1 to 85 amino acids in sequence or an amino acid (Asp-), as represented by Z. Typical examples of such proteins are polypeptides I, II, III and IV given below by the primary structures.

Polypeptide I

Ala Pro Val Arg Ser Leu Asn Cys Thr Leu Arg
Asp Ser Gln Gln Lys Ser Leu Val Met Ser Gly
Pro Tyr Glu Leu Lys Ala Leu His Leu Gln Gly
Gln Asp Met Glu Gln Gln Val Val Phe Ser Met
Ser Phe Val Gln Gly Glu Glu Ser Asn Asp Lys
Ile Pro Val Ala Leu Gly Leu Lys Glu Lys Asn
Leu Tyr Leu Ser Cys Val Leu Lys Asp Asp Lys
Pro Thr Leu Gln Leu Glu Ser Val Asp Pro Lys
Asn Tyr Pro Lys Lys Lys Met Glu Lys Arg Phe
Val Phe Asn Lys Ile Glu Ile Asn Asn Lys Leu
Glu Phe Glu Ser Ala Gln Phe Pro Asn Trp Tyr
Ile Ser Thr Ser Gln Ala Glu Asn Met Pro Val
Phe Leu Gly Gly Thr Lys Gly Gly Gln Asn Ile
Thr Asp Phe Thr Met Gln Phe Val Ser Ser

Polypeptide II

Met Leu Val Pro Cys Pro Gln Thr Phe Gln Glu
Asn Asp Leu Ser Thr Phe Phe Pro Phe Ile Phe
Glu Glu Glu Pro Ile Phe Phe Asp Thr Trp Asp
Asn Glu Ala Tyr Val His Asp Ala Pro Val Arg
Ser Leu Asn Cys Thr Leu Arg Asp Ser Gln Gln
Lys Ser Leu Val Met Ser Gly Pro Tyr Glu Leu
Lys Ala Leu His Leu Gln Gly Gln Asp Met Glu
Gln Gln Val Val Phe Ser Met Ser Phe Val Gln
Gly Glu Glu Ser Asn Asp Lys Ile Pro Val Ala
Leu Gly Leu Lys Glu Lys Asn Leu Tyr Leu Ser
Cys Val Leu Lys Asp Asp Lys Pro Thr Leu Gln
Leu Glu Ser Val Asp Pro Lys Asn Tyr Pro Lys
Lys Lys Met Glu Lys Arg Phe Val Phe Asn Lys
Ile Glu Ile Asn Asn Lys Leu Glu Phe Glu Ser
Ala Gln Phe Pro Asn Trp Tyr Ile Ser Thr Ser
Gln Ala Glu Asn Met Pro Val Phe Leu Gly Gly
Thr Lys Gly Gly Gln Asp Ile Thr Asp Phe Thr
Met Gln Phe Val Ser Ser

Polypeptide III

Met Asp Lys Leu Arg Lys Met Leu Val Pro Cys
Pro Gln Thr Phe Gln Glu Asn Asp Leu Ser Thr
Phe Phe Pro Phe Ile Phe Glu Glu Glu Pro Ile
Phe Phe Asp Thr Trp Asp Asn Glu Ala Tyr Val
His Asp Ala Pro Val Arg Ser Leu Asn Cys Thr
Leu Arg Asp Ser Gln Gln Lys Ser Leu Val Met
Ser Gly Pro Tyr Glu Leu Lys Ala Leu His Leu
Gln Gly Gln Asp Met Glu Gln Gln Val Val Phe
Ser Met Ser Phe Val Gln Gly Glu Glu Ser Asn
Asp Lys Ile Pro Val Ala Leu Gly Leu Lys Glu
Lys Asn Leu Tyr Leu Ser Cys Val Leu Lys Asp
Asp Lys Pro Thr Leu Gln Leu Glu Ser Val Asp
Pro Lys Asn Tyr Pro Lys Lys Lys Met Glu Lys
Arg Phe Val Phe Asn Lys Ile Glu Ile Asn Asn
Lys Leu Glu Phe Glu Ser Ala Gln Phe Pro Asn
Trp Tyr Ile Ser Thr Ser Gln Ala Glu Asn Met
Pro Val Phe Leu Gly Gly Thr Lys Gly Gly Gln
Asp Ile Thr Asp Phe Thr Met Gln Phe Val Ser
Ser

Polypeptide IV

Met Lys Cys Ser Phe Gln Asp Leu Asp Leu Cys
Pro Leu Asp Gly Gly Ile Gln Leu Arg Ile Ser
Asp His His Tyr Ser Lys Gly Phe Arg Gln Ala
Ala Ser Val Val Val Ala Met Asp Lys Leu Arg
Lys Met Leu Val Pro Cys Pro Gln Thr Phe Gln
Glu Asn Asp Leu Ser Thr Phe Phe Pro Phe Ile
Phe Glu Glu Glu Pro Ile Phe Phe Asp Thr Trp
Asp Asn Glu Ala Tyr Val His Asp Ala Pro Val

-continued

Arg Ser Leu Asn Cys Thr Leu Arg Asp Ser Gln
Gln Lys Ser Leu Val Met Ser Gly Pro Tyr Glu
Leu Lys Ala Leu His Leu Gln Gly Gln Asp Met
Glu Gln Gln Val Val Phe Ser Met Ser Phe Val
Gln Gly Glu Glu Ser Asn Asp Lys Ile Pro Val
Ala Leu Gly Leu Lys Glu Lys Asn Leu Tyr Leu
Ser Cys Val Leu Lys Asp Asp Lys Pro Thr Leu
Gln Leu Glu Ser Val Asp Pro Lys Asn Tyr Pro
Lys Lys Lys Met Glu Lys Arg Phe Val Phe Asn
Lys Ile Glu Ile Asn Asn Lys Leu Glu Phe Glu
Ser Ala Gln Phe Pro Asn Trp Tyr Ile Ser Thr
Ser Gln Ala Glu Asn Met Pro Val Phe Leu Gly
Gly Thr Lys Gly Gly Gln Asp Ile Thr Asp Phe
Thr Met Gln Phe Val Ser Ser

As will be described later, one of the GIF of the present invention can be isolated from immunologically competent cells of mammals as a natural GIF. Genetic analysis has revealed that there is a precursor for the natural GIF. The amino acid sequences of polypeptide A of the formula (1) and of polypeptides I to IV are determined by the result of the genetic analysis.

The GIF's of the present invention include those having a protein primary structure wherein one or more amino acids is attached to the N-terminal or C-terminal of the amino acid sequence of one of polypeptide A and polypeptides I to IV, or wherein at least one amino acid is eliminated from or substituted for the amino acid sequence, provided that the active substances have GIF activity.

The GIF of the present invention will be described below in detail with reference to a process for preparing the same.

The GIF of the present invention is derived and produced by the culture of immunologically competent cells from mammals. The immunologically competent cells to be used are not limited specifically insofar as they are derived from mammals. Useful mammals are not limited either, and include man, ox or cow, swine, goat, horse, rabbit, mouse, etc. Typical examples of immunologically competent cells are T-cells, B-cells, null cells, natural killer cells and like lymphocytes, mononuclear cells, macrophages and like mononuclear cells, and cell lines of such cells. Examples of lymphocytes are those removed from the spleen, tonsil, lung, blood, lymphnode or lymphoid tissues of the above mammals. Such immunologically competent cells can be separated off by a usual method, for example, by crushing a tissue containing the desired cells, filtering off extraneous matter and collecting the cells by centrifugation.

Our research has revealed that the GIF activity has no species specificity irrespective of the kind of immunologically competent cells used as the starting cells or the kind of mammal providing the cells. Accordingly, the starting cells to be used for preparing the GIF of the invention are not limited, and in this respect, the invention is advantageous for application to the field of therapy.

The various immunologically competent cells mentioned above are incubated using culture media which are generally used for a culture of such cells, preferably in the presence of an antitumor substance inducing agent. The substance of the invention is obtained in the supernatant of the culture. Examples of useful culture media are CEM medium, CMRL-1066 medium, DM-160 medium, Eagle's MEM, autoclavable MEM, Fisher's medium, F-10 and F-12 media, L-15 medium, NCTC-109 medium, RPMI-1640 medium and the like.

These media are used singly, or when desired, the medium may contain serum such as fetal bovine serum (FCS), or a serum component such as albumin. For incubation, immunologically competent cells are used preferably in an amount of about $1 \times 10^4$ to about $1 \times 10^7$ cells/ml based on the medium.

Antitumor substance inducing agents which can be incorporated into the cell suspension are those usually used, such as 12-O-tetradecanoylphorbol-13 acetate (TPA), phytohemagglutinin (PHA), concanavalin A (ConA), bacterial lipopolysaccharide (LPS), pokeweed mitogen (PWM), protein A (ProteinA) and the like. These agents are used in a concentration usually of 0.0001 to 0.1% (W/V %, same as hereinafter), preferably about 0.001%. Incubation can be conducted by a usual method, for example, by using $CO_2$ incubator. Incubation is carried out at about 30 to about 40° C., preferably about 37° C., for 1 to 5 days. After the incubation, the culture supernatant is separated off by a usual method, as by centrifugation.

The GIF of the present invention can be separated from the supernatant substantially by the same method as usually used for separating a protein-like substance from such a biological substance. For example, various procedures are usable utilizing the physical or chemical properties of the desired GIF. (See for example, "Biological Data Book II," pp. 1175-1259, 1st edition, 1st print, June 23, 1980, published by Kabushiki Kaisha Tokyo Kagakudojin.) Examples of useful procedures are treatment with use of a usual protein precipitating agent, ultrafiltration, molecular sieve chromatography (gel filtration), liquid chromatography, centrifugation, electrophoresis, affinity chromatography, dialysis, and combinations of such procedures.

According to a preferred method of separation, the desired GIF is separated from the supernatant as partially purified. This partial purification is carried out, for example, by a treatment using as a protein precipitating agent an organic solvent such as acetone, methanol, ethanol, propanol or dimethylformamide (DMF), or an acidic reagent such as acetic acid, perchloric acid (PCA) or trichloroacetic acid (TCA), a treatment using a salting-out agent such as ammonium sulfate, sodium sulfate or sodium phosphate and/or ultrafiltration using a dialysis membrane, flat membrane, hollow fiber membrane or the like. These treatments are conducted in the same manner as usually done under usual conditions.

The roughly purified product thus obtained is then subjected to gel filtration, whereby a fraction exhibiting the activity of the desired substance is collected. Useful gel filtration agents are not limited specifically. Such agents include those made of dextran gel, polyacrylamide gel, agarose gel, polyacrylamideagarose gel, cellulose or the like. Examples of useful agents commercially available are Sephadex G type, Sephadex LH type, Sepharose type, Sephacryl type (all products of Pharmacia), Cellofine (Chisso Corporation), Biogel P type, Biogel A type (both product of LKB), TSK-G type (product of Toyo Soda Mfg. Co., Ltd.), etc.

The gel filtration procedure gives a fraction of 10,000 to 25,000 in molecular weight exhibiting the activity of the substance of the invention.

The substance of the present invention can be isolated from the fraction as a homogeneous substance, for example, by subjecting the fraction to affinity chromatography with use of a hydroxyapatite column, ion exchange column chromatography as the DEAE method, chromatofocusing method, reverse-phase high-performance liquid chromatography or the like, or to a combination of such methods.

The chromatofocusing method can be carried out by various known procedures. Usable as the column is, for example, PBE94 (Pharmacia) or the like, as the starting buffer, for example, imidazole-hydrochloric acid or the like, and the eluent, for examle, the mixture of Polybuffer 74 (Pharmacia) and hydrochloric acid (pH 4.0) or the like.

The reverse-phase high-performance liquid chromatography can be conducted, for example, with $C_4$ Hi-Pore reverse-phase HPLC column (Bio-Rad Laboratories) or the like, using acetonitrile, trifluoroacetic acid (TFA), water of the like, or a mixture of such solvents as the eluent.

The GIF thus obtained is of the natural type (i.e., mature GIF) comprising polypeptide I as its constituent protein.

The GIF of the present invention can also be prepared by a genetic engineering technique using a gene coding for the GIF, i.e., by introducing the gene into a vector of a microorganism, followed by replication, transcription and translation within microorganic cells. This process has the advantage of being amenable to quantity production.

The gene to be used for preparing the GIF by the genetic engineering technique is characterized in that it codes for the GIF. The present invention provides this novel gene.

While typical of such a gene is one coding for polypeptide A, especially polypeptide I, the usable gene is not limited thereto. Any gene is useful which codes for the GIF of the invention and which is usable for expressing and preparing the GIF. Various known genetic codes are also usable.

Useful genes include those which are prepared from messenger RNA (hereinafter referred to as "mRNA") separated from human lymphoid cell series and which are characterized in that the DNA chain thereof has sites where it is to be cleaved with restriction enzymes MspI, HindIII and PvuII and which are arranged in this order. More specifically, these genes have nucleotide sequences which are defined as nucleotide sequences I, II, III and IV given below and corresponding to polypeptides I to IV.

Nucleotide sequence I

| | | | | | | |
|---|---|---|---|---|---|---|
| GCA | CCT | GTA | CGA | TCA | CTG | AAC TGC |
| ACG | CTC | CGG | GAC | TCA | CAG | CAA AAA |
| AGC | TTG | GTG | ATG | TCT | GGT | CCA TAT |
| GAA | CTG | AAA | GCT | CTC | CAC | CTC CAG |
| GGA | CAG | GAT | ATG | GAG | CAA | CAA GTG |
| GTG | TTC | TCC | ATG | TCC | TTT | GTA CAA |
| GGA | GAA | GAA | AGT | AAT | GAC | AAA ATA |
| CCT | GTG | GCC | TTG | GGC | CTC | AAG GAA |
| AAG | AAT | CTG | TAC | CTG | TCC | TGC GTG |
| TTG | AAA | GAT | GAT | AAG | CCC | ACT CTA |
| CAG | CTG | GAG | AGT | GTA | GAT | CCC AAA |
| AAT | TAC | CCA | AAG | AAG | ATG | GAA |
| AAG | CGA | TTT | GTC | TTC | AAC | AAG ATA |
| GAA | ATC | AAT | AAC | AAG | CTG | GAA TTT |
| GAG | TCT | GCC | CAG | TTC | CCC | AAC TGG |
| TAC | ATC | AGC | ACC | TCT | CAA | GCA GAA |
| AAC | ATG | CCC | GTC | TTC | CTG | GGA GGG |
| ACC | AAA | GGC | GGC | CAG | GAT | ATA ACT |
| GAC | TTC | ACC | ATG | CAA | TTT | GTG TCT |
| TCC | | | | | | |

Nucleotide sequence II

```
ATG  CTG  GTT  CCC  TGC  CCA  CAG  ACC
TTC  CAG  GAG  AAT  GAC  CTG  AGC  ACC
TTC  TTT  CCC  TTC  ATC  TTT  GAA  GAA
GAA  CCT  ATC  TTC  TTC  GAC  ACA  TGG
GAT  AAC  GAG  GCT  TAT  GTG  CAC  GAT
GCA  CCT  GTA  CGA  TCA  CTG  AAC  TGC
ACG  CTC  CGG  GAC  TCA  CAG  CAA  AAA
AGC  TTG  GTG  ATG  TCT  GGT  CCA  TAT
GAA  CTG  AAA  GCT  CTC  CAC  CTC  CAG
GGA  CAG  GAT  ATG  GAG  CAA  CAA  GTG
GTG  TTC  TCC  ATG  TCC  TTT  GTA  CAA
GGA  GAA  GAA  AGT  AAT  GAC  AAA  ATA
CCT  GTG  GCC  TTG  GGC  CTC  AAG  GAA
AAG  AAT  CTG  TAC  CTG  TCC  TGC  GTG
TTG  AAA  GAT  GAT  AAG  CCC  ACT  CTA
CAG  CTG  GAG  AGT  GTA  GAT  CCC  AAA
AAT  TAC  CCA  AAG  AAG  AAG  ATG  GAA
AAG  CGA  TTT  GTC  TTC  AAC  AAG  ATA
GAA  ATC  AAT  AAC  AAG  CTG  GAA  TTT
GAG  TCT  GCC  CAG  TTC  CCC  AAC  TGG
TAC  ATC  AGC  ACC  TCT  CAA  GCA  GAA
AAC  ATG  CCC  GTC  TTC  CTG  GGA  GGG
ACC  AAA  GGC  GGC  CAG  GAT  ATA  ACT
GAC  TTC  ACC  ATG  CAA  TTT  GTG  TCT
TCC
```

Nucleotide sequence III

```
ATG  GAC  AAG  CTG  AAG  AAG  ATG  CTG
GTT  CCC  TGC  CCA  CAG  ACC  TTC  CAG
GAG  AAT  GAC  CTG  AGC  ACC  TTC  TTT
CCC  TTC  ATC  TTT  GAA  GAA  GAA  CCT
ATC  TTC  TTC  GAC  ACA  TGG  GAT  AAC
GAG  GCT  TAT  GTG  CAC  GAT  GCA  CCT
GTA  CGA  TCA  CTG  AAC  TGC  ACG  CTC
CGG  GAC  TCA  CAG  CAA  AAA  AGC  TTG
GTG  ATG  TCT  GGT  CCA  TAT  GAA  CTG
AAA  GCT  CTC  CAC  CTC  CAG  GGA  CAG
GAT  ATG  GAG  CAA  CAA  GTG  GTG  TTC
TCC  ATG  TCC  TTT  GTA  CAA  GGA  GAA
GAA  AGT  AAT  GAC  AAA  ATA  CCT  GTG
GCC  TTG  GGC  CTC  AAG  GAA  AAG  AAT
CTG  TAC  CTG  TCC  TGC  GTG  TTG  AAA
GAT  GAT  AAG  CCC  ACT  CTA  CAG  CTG
GAG  AGT  GTA  GAT  CCC  AAA  AAT  TAC
CCA  AAG  AAG  AAG  ATG  GAA  AAG  CGA
TTT  GTC  TTC  AAC  AAG  ATA  GAA  ATC
AAT  AAC  AAG  CTG  GAA  TTT  GAG  TCT
GCC  CAG  TTC  CCC  AAC  TGG  TAC  ATC
AGC  ACC  TCT  CAA  GCA  GAA  AAC  ATG
CCC  GTC  TTC  CTG  GGA  GGG  ACC  AAA
GGC  GGC  CAG  GAT  ATA  ACT  GAC  TTC
ACC  ATG  CAA  TTT  GTG  TCT  TCC
```

Nucleotide sequence IV

```
ATG  AAG  TGC  TCC  TTC  CAG  GAC  CTG
GAC  CTC  TGC  CCT  CTG  GAT  GGC  GGC
ATC  CAG  CTA  CGA  ATC  TCC  GAC  CAC
CAC  TAC  AGC  AAG  GGC  TTC  AGG  CAG
GCC  GCG  TCA  GTT  GTT  GTG  GCC  ATG
GAC  AAG  CTG  AGG  AAG  ATG  CTG  GTT
CCC  TGC  CCA  CAG  ACC  TTC  CAG  GAG
AAT  GAC  CTG  AGC  ACC  TTC  TTT  CCC
TTC  ATC  TTT  GAA  GAA  GAA  CCT  ATC
TTC  TTC  GAC  ACA  TGG  GAT  AAC  GAG
GCT  TAT  GTG  CAC  GAT  GCA  CCT  GTA
CGA  TCA  CTG  AAC  TGC  ACG  CTC  CGG
GAC  TCA  CAG  CAA  AAA  AGC  TTG  GTG
ATG  TCT  GGT  CCA  TAT  GAA  CTG  AAA
GCT  CTC  CAC  CTC  CAG  GGA  CAG  GAT
ATG  GAG  CAA  CAA  GTG  GTG  TTC  TCC
ATG  TCC  TTT  GTA  CAA  GGA  GAA  GAA
AGT  AAT  GAC  AAA  ATA  CCT  GTG  GCC
TTG  GGC  CTC  AAG  GAA  AAG  AAT  CTG
TAC  CTG  TCC  TGC  GTG  TTG  AAA  GAT
GAT  AAG  CCC  ACT  CTA  CAG  CTG  GAG
AGT  GTA  GAT  CCC  AAA  AAT  TAC  CCA
AAG  AAG  AAG  ATG  GAA  AAG  GGA  TTT
GTC  TTC  AAC  AAG  ATA  GAA  ATC  AAT
AAC  AAG  CTG  GAA  TTT  GAG  TCT  GCC
CAG  TTC  CCC  AAC  TGG  TAC  ATC  AGC
ACC  TCT  CAA  GCA  GAA  AAC  ATG  CCC
GTC  TTC  CTG  GGA  GGG  ACC  AAA  GGC
GGC  CAG  GAT  ATA  ACT  GAC  TTC  ACC
ATG  CAA  TTT  GTG  TCT  TCC
```

The method of preparing the gene to be used for the process of the invention is not limited specifically but can be any of the following methods. The cDNA prepared, for example, from mRNA obtained from lymphoid cell series having ability to produce GIF is joined to a suitable vector, such as plasmid of *E. coli*, and amplified in cells of a microorganism to isolate clones capable of expressing GIF, and cDNA is separated from the plasmids contained in the isolated clones. As another method chemical synthesis such as the phosphite-triester method (*Nature*, 310, 105 (1984)) is available. The method is conducted based on the information of GIF and gene thereof disclosed herein. These methods may be employed in combination.

In the above methods, the genetic code may be selected as desired in the usual manner considering, for example, the frequency of codon usage in the host. Substitution of part of the amino acid and alternation of the amino acid sequence of the GIF gene are suitably carried out by usual method, for example Site-Specific Mutagenesis described in Proc. Natl. Acad. Sci., 81, 5662–5666 (1984).

The method of preparing the gene from the mRNA will be described below in greater detail.

Suitable starting cells for preparing the gene of the present invention are immunologically competent cells derived from mammals and having ability to produce GIF (i.e. GIF producing cells). Examples of useful cells are already mentioned.

The RNA containing mRNA coding for the GIF is extracted from GIF producing cells in the usual manner. Before extraction, the GIF producing cells are generally subjected to GIF producing condition, that is, the cells are incubated in a medium which is commonly used for incubating cells of this type, preferably in the presence of an antitumor substance inducing agent. Suitable medium, amount of the cells relative to the medium, inducing agent, amount thereof, incubation method, etc. can be determined according to what has already been described. RNA is extracted from the cells obtained about the time when GIF activity appears in the culture supernatant.

The RNA is extracted by partially or completely breaking down and solubilizing the cells using a suitable detergent, such as SDS, NP-40, triton X100, deoxychloic acid or the like, or a homogenizer, freeze-thaw or like physical method, thereafter shearing chromosome DNA to some extent usin POLYTORON model CH-6010 (product of Kinematica, Switzerland) or like mixer or syringe barrel, and subsequently separating a nucleic acid fraction from protein. Generally used for this procedure is the CsCl method (Glisin, V. et al., Biochemistry, 13, 2633 1974)) resorting to phenolchloroform extraction or ultracentrifugation (Chirgwin, J. M. et al., Biochemistry, 18, 5294 (1979)).

To prevent destruction of RNA by RNase in the above method, it is desirable to add an RNase inhibitor such as heparin, polyvinylsulfuric acid, diethyl pyrocarbonate, vanadyl ribonucleoside complex, bentonite, Macaloid or the like.

mRNA can be separated from the resulting RNA extract by a batchwise method or with use of an adsporption column such as Oligo dT-Cellulose (Collaborative Research Inc.), Poly U-Sepharose (Pharmacia), Sepharose 2B (Pharmacia) or the like.

The desired mRNA can be obtained from the resulting mRNA in a pure concentration form and identified, for example, by precipitating mRNA from the polysome with use of an antibody of GIF. Alternatively, the presence of the desired mRNA can be confirmed by fractionating the mRNA by sucrose density gradient centrifugation or the like, translating the fraction into protein by injecting into *Xenopus laevis* oocyte or using cell-free system such as rabbit reticulocytes lysates or wheat germ extracts and checking the protein for GIF activity. Further alternatively, the desired mRNA can be identified by immunological method with use of an antibody against GIF.

The pure mRNA thus obtained, which is usually unstable, is converted to stable complementary DNA (cDNA) and joined to a replicon derived from a microorganism to make possible the amplification of the desired gene. The conversion of mRNA to cDNA, i.e., synthesis of cDNA, *in vitro* can be conducted generally in the following manner.

First, using oligo dT as a primer (which may be free oligo dT or oligo dT already attached to a vector primer) and using mRNA as a template, a single-stranded cDNA complementary to mRNA is prepared in the presence of dNTP (dATP, dGTP, dCTP or dTTP) with use of a reverse transcriptase. The next step differs as follows depending on which of the free oligo dT and the other oligo dT is used in the above step.

When the former is used, the mRNA used as the template is decomposed with an alkali or the like and removed, and double stranded DNA is prepared with a transcriptase or DNA polymerase using the single stranded DNA as a template. This is followed by treating both ends of the double stranded DNA with exonuclease, attaching a suitable linker DNA or a combination of bases that can be annealed to each end, and incorporating the assembly into a suitable vector, such as EX-type plasmid vector (of the stringent type or relax type), or λgt-phage vector.

When the latter is used, a complete plasmid DNA can be prepared by annealing a linearized plasmid having the same linker as above attached thereto, and linker DNA (a DNA fragment is often used which has a region that can be autonomously replicated in animal cells, and a transcription promotor region for mRNA) to form the circle while allowing the template mRNA to remain, and replacing the mRNA by DNA strand in the presence of dTNP, RNase and DNA polymerase.

The DNA thus obtained is introduced into a host microorganism for the vector for transformation.

Typical of useful host microorganism is *E. coli*, which, however, is not limitative. Also usable are *Bacillus subtilis*, *Saccharomyces cerevisiae*, etc.

The DNA can be introduced into the host for transformation by a method commonly used. For example, cells mainly in the logarithmic growth phase are collected and treated with $CaCl_2$ to render them ready to accept DNA spontaneously. To effect transformation with an improved efficiency, this method can be practiced further in the presence of $MgCl_2$ or RbCl as generally known. It is also possible to convert the cell to spheroplast or protoplast before transformation.

The strain containing DNA of the desired GIF can be selected from the transformants thus obtained, for example, by methods given below.

(1) Screening method using a synthesized oligonucleotide probe

When the amino acid sequence of the desired protein is entirely or partly known (any region of the desired protein provided that the sequence is a specific series of amino acids), an oligonucleotide corresponding to the amino acids is prepared (in this case, either of the base sequence derived with use of codon usage frequency, or a plurality of combinations of possible base sequences; in the latter case; the number of combination can be reduced by incorporating inosine). The oligonucleotide serving as a probe (as labelled with $^{32}P$ or $^{35}S$) is hybridized with a nitrocellulose filter having the DNA's of transformants fixed thereto on denaturation, and the resulting positive strain is retrieved for selection.

(2) Screening method wherein GIF is produced in animal cells

This method comprises incubating the transformant to amplify the gene, transfecting the gene in animal cells (i.e., plasmids which can be autonomously replicated and contain mRNA transcription promotor region, or plasmids which will intergrate in the chromosome of animal cells) to cause the cells to produce the protein encoded in the gene, and checking the culture supernatant or the extract from the incubated cells for GIF activity or detecting the GIF therefrom with use of an antibody against the GIF. By repeating this method for the original transformants, a strain can be identified which has cNDA coding for the desired GIF.

(3) Method of selecting induction-specific transformant

As already described, production of GIF is induced by an antitumor substance inducing agent, such as LPS, TPA or the like.

An induction-specific strain is selected using mRNA from a strain wherein no GIF is induced (induction minus) and amplified mRNA inducing GIF with use of the agent (induction plus) and coding for the GIF (mRNA may be replaced by cDNA prepared therefrom) as colony hybridization probes. These mRNS's are hybridized to determine the stronger of the two to select the induction-specific strain (plus-minus method).

Further induction-minus mRNA (or cDNA prepared therefrom) and cDNA prepared from induction-plus mRNA (or mRNA per se) are hybridized, and colony hybridization is thereafter conducted using the non-hybridized mRNA (or cDNA) as a probe to select an induction-specific strain (selective hybridization method).

The desired strain can be selected with reference to cDNA or mRNA.

(4) Method of selection with use of antibody against GIF cDNA is incorporated into a vector capable of expressing protein in the transformant, the transformants are cause to produce protein therein, and the GIF producing strain is detected using an antibody against GIF and a second antibody against the antibody.

(5) Method using selective hybridization-translation system cDNA obtained from the transformant is blotted on a nitrocellulose filter or the like, mRNA from GIF producing cells is hybridized therewith, and mRNA corresponding to cDNA is collected, which is then translated into protein using a protein translation system, for example, injecting into *Xenopus laevis* oocytes or using a cell-free system such as rabbit reticulocytes lysates or wheat germ extracts. The protein is then checked for GIF activity, or the protein concerned is detected with use of an antibody against GIF, whereby the desired strain can be identified.

The DNA coding for the GIF can be collected from the desired transformant by a known method, for example, by separating a fraction corresponding to plasmid DNA from the cells and cutting out cDNA region from the plasmid DNA.

The nucleotide sequence of cDNA of the GIF can be determined, for example, by the chemical modification method of Maxam and Gilbert (Meth. Enzym. 65, 499–560 (1980)) and the dideoxynucleotide chain termination method with use of M13 phage (Messing, J. and Vieira, J., Gene, 19, 269–276 (1982)).

One of the transformant thus obtained is *E. coli* X1776 transformant harboring plasmid pGIF-α containing cDNA of GIF. This transformant, termed (Escherichia coli X1776/pGIF-α, is deposited with deposition number FERM BP-948 in Fermentation Research Institute, Agency of Industrial Science and Technology since Dec. 12, 1985. Accordingly, the GIF gene can be prepared easily and advantageously with use of this transformant.

A large amount of GIF can be obtained by gene manipulation technique using the gene coding for GIF. The technique provides a recombinant DNA capable of expressing the gene in the host cell by a method conventional in the art. The recombinant DNA can be easily prepared based on the genetic information as to GIF herein disclosed. The specific procedures for the preparation, although partly described already, will be described below in greater detail.

Useful hosts cells can be either eucaryotic or procaryotic cells. The eucaryotic cells include cells of vertebrate animals, yeasts, etc. Generally used as cells of vertebrate animals are, for example, Cos cells which are cells of monkey (Y. Gluzman, Cell, 23, 175–182 (1981)), dihydrofolic acid reductase defective strain of Chinese hamster ovearian cell (G. Urlaub and L. A., Chasin, Proc. Natl. Acad. Sci., U.S.A., 77, 4216–4220 (1980)), etc., while useful cells are not limited to these cells. Useful expression vectors of vertebrate cells are those having a promotor positioned upstream of the gene to be expressed, RNA splicing sites, polyadenylation site, transcription termination sequence, etc. These vectors may further have a duplication origin when required. Examples of useful expression vectors include pSV2dhfr having an initial promotor of SV40 (S. Sabramani, R. Mulligan and P. Berg, Mol. Cell. Biol., 1, 854–764), which is not limitative.

Yeasts are widly used as eucaryotic microorganisms, among which those of the genus Saccharomyces are generally usable. Examples of popular expression vectors of yeasts and like eucaryotic microorganisms include pAM82 having a promotor for acid phosphatase gene (A. Miyanohara et al., Proc. Natl. Acad. Sci., U.S.A., 80, 1–5 (1983), etc.

*E. coli* and *Bacillus subtilis* are generally used as procaryotic hosts. The present invention employs, for example plasmid vectors capable of duplication in the host. To express the GIF gene in the vector, expression plasmids can be used which have a promotor and SD (Shine-Dalgarno) base sequence at the upstream of the GIF gene and ATG required for initiating protein synthesis. Widely used as host *E. coli* is *E. coli* K12 strain. pBR322 is a vector which is generally used. However, these are not limitative, and various known strains and vectors are usable. Examples of promotors usable are tryptophan promotor, $P_L$ promotor, lac promotor, lpp promotor, etc. The GIF gene can be expressed with use of any of these promotors.

To describe the procedure with reference to the case wherein tryptophan promotor is used, vector pTM1 (Fumio Imamoto, Metabolism, Vol. 22, 289 (1985)) having tryptophan promotor and SD sequence is used as an expression vector. A gene coding for GIF and having ATG when required is linked to the site of restriction enzyme ClaI which is present downstream from the SD sequence. Stated more specifically for the preparation of polypeptide I, for example, by this method, plasmid pGIF-α given in the example to follow and having cDNA of GIF is cleaved with restriction enzymes AccI and MspI to obtain an isolated DNA fragment having a major portion of the gene coding for polypeptide I and a portion of 3' non-translation region. This DNA fragment is deficient in the gene region coding for ten amino acid residues toward the amino terminal of polypeptide I. With the above method, therefore, a synthetic DNA linker is subsequently prepared which can be linked to the site of restriction enzyme ClaI in expression vector pTM1 having tryptophan promotor, has translation start codon ATG and capable of coding for the ten amino acid residues at the amino terminal end of polypeptide I. With use of the linker, the gene of polypeptide I is inserted downstream of the tryptophan promotor to prepare an expression plasmid. By transformation, the plasmid is introduced into *E. coli* which is made ready to accept DNA by treatment with $CaCl_2$. The desired transformant is incubated by a usual method to obtain polypeptide I. The incubation of the transformant is conducted generally with use of M9 minimum medium having incorporated therein Casamino acid to assure the action of tryptophan promotor. It is also possible to add to the medium a chemical, such as indoleacrylic acid, for intensifying the action of the tryptophan promotor, at a suitable time during incubation. A large quantity of polypeptide I is produced and accumulated in *E. coli* thus incubated.

The processes of the invention for preparing GIF other than the above process can be practiced similarly.

The GIF produced within or outside the cells of the desired recombinant microorganism can be separated off in the usual manner and further isolated and purified by various procedures utilizing physical or chemical properties of GIF, as already exemplified above.

The GIF obtained by the present process is useful as it is as an antitumor agent for man and other animals because of its GIF activity and action to specifically inhibit the growth of various tumor cells. It is advantageously usable for the chemotherapy of cancers, especially for remission intensifying therapy and and remission maintaining therapy in combination with various drugs for treating malignant tumors. Because of its extremely low toxicity, the GIF is advantageous to the above use.

For use as an antitumor agent, the GIF is formulated into pharmacological compositions containing an effective amount of GIF and a usual nontoxic carrier. The composition is given via a route of administration suited to the form of the composition. Such compositions are, for example, in the form of usual liquid preparations including solution, suspension, emulsion and the like, which are given usually orally, intravenously, subcutaneously or intramuscularly. The composition can be provided also as a dry preparation which can be reconstituted to a liquid for use by addition of a suitable common carrier. While the amount of the composition to be given differs with the age and sex of the patient, degree of disease, etc. The composition is administered preferably at a dose of about 0.1 to about 100 mg/kg/day, calculated as protein, dividely.

The present invention will be described in greater detail with reference to the following examples.

The GIF activity was determined by the following method.

DETERMINATION OF GIF ACTIVITY

Portions (0.1 ml) of the test solution diluted to varying concentrations were placed into the wells of 96-well microplate (Corning Co., Ltd.), 0.1 ml of Eagle's MEM suspension containing 10% FCS containing human melonoma cells A375 in an amount of $2 \times 10^4$ cells/ml was then placed into each well, and the cells were incubated in a $CO_2$ incubator (Napco Co., Ltd.) for 4 days. After the incubation, 0.05 ml of 0.05% Neutral Red (Wako Junyaku Co., Ltd.) was placed into each well, followed by incubation at 37° C. for 2 hours. After removing the supernatant, 0.3 ml of phosphoric acid buffer saline was gently poured into each well for washing. After removing the washing, 0.1 ml of mixture of sodium dihydrogenphosphate and ethanol in equal amounts was placed into each well, the plate was shaken for several minutes by a micromixer, and the amount of pigment taken into the cell was measured at an absorbance of 540 m$\mu$ using a photometer for 96-well microtitration plates (Titer check multiscane, Flow Lab.) to determine growth inhibition activity. The test group exhibiting 50% of the inhibition of cell growth of the control group, i.e., the test group which exhibited ½ the absorbance measured of the control group, was identified. The reciprocal of the number of times of dilution for the test group was taken as the GIF activity unit. Accordingly, when the GIF activity is 10 units, for example, the test solution, if diluted tenfold, still has activity to inhibit cell growth 50%.

EXAMPLE 1

(I) Preparation of Natural Type GIF

Human peripheral blood lymphocytes were suspended in RPMI-1640 containing 2% FCS to prepare a cell suspension containing $1 \times 10^6$ cells/ml.

PHA-P (kidyney bean lectin, product of Difco), serving as an antitumor substance inducing agent, was added to the suspension at a concentration of 0.2%, followed by incubation in a $CO_2$ incubator (NAPCO5300, Napco Co., Ltd.) at 37° C. for 3 days. The culture was centrifuged (2000 g$\times$10 min) to obtain a supernatant, which was thereafter used as the starting liquid.

The starting liquid was fractionated by the ammonium sulfate precipitation method (Nippon Seikagaku-kai edited, "Seikagaku Jikken Koza", Vol. 1, Tokyo Kagakudojin).

A precipitate having GIF activity was found in fractions having an ammonium sulfate concentration of 50 to 80%.

The precipitate was subjected to AcA54 (LKB) gel chromatography (80 cm$\times$4.4 cm (diam.), mobile phase: phosphate buffer saline containing 0.02% polyethylene glycol (molecular weight 6000), flow rate 30 ml/hr) to obtain a fraction with a molecular weight of 10,000 to 25,000 which had GIF activity. This fraction exhibited no TNF, IFN or CSF activity.

Figure 1:
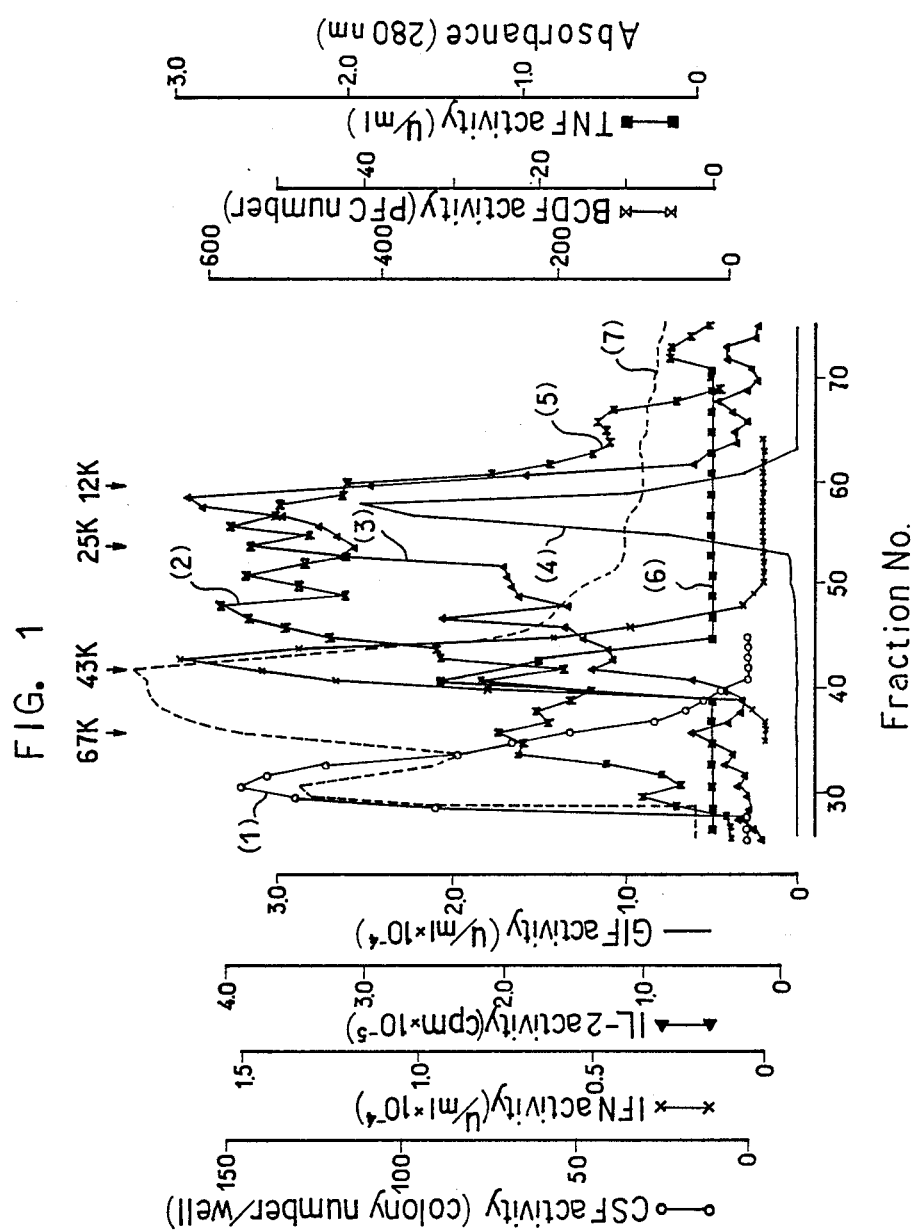
FIG. 1 shows cell chromatographic results.

FIG. 1 shows the results of gel chromatography. In the diagram, the fraction number is plotted as abscissa vs. the physiological activities and the absorbance with $OD_{280}$ as ordinate. Further for reference, the diagram shows the molecular weight corresponding to each fraction along with an arrow. In the diagram, CSF activity is represented by curve (1), IFN activity by curve (2), IL-2 activity by curve (3), GIF activity of the invention by curve (4), BCDF activity by curve (5), TNF activity by curve (6), and absorbance by curve (7).

Determination of activity

Physiological activities were determined by the following methods.

*GIF

According to the foregoing method.

*TNF

By the method of A. Khan et al. (Human Lymphokines, Academic Press, pp. 23-32, (1982)) using L929 cell strain.

*IFN

By the method of Sudo et al. (Tetsuo Sudo, Reiko Ohkubo, Masahiko Iizuka and Shigeyasu Kobayashi, 42nd Virus Yokusei Inshi Kenkyukai, 1982; Kohase; M., S. Kohno and S. Yamazaki (1982), Potency standardization of human IFN preparation for clinical trials. In the clinical potential for interferons, edt. by Kohno, p299, Tokyo University press.) using a system including human amino-derived FL cells and Sindbis virus.

*CSF (colony stimulating factor)

By the method of J. J. Farrar et al. (J. Immunol., 127, 1983 (1981)) using myeloid cells of BALB/c mouse.

*LAF (lymphocyte activation factor)

By the method of J. J. Oppenhein et al. (J. Immunol., 116, 1466 (1976)) using thymocytes of C3H/HeJ mouse.

*IL-2 (interleukin-2)

By the method of S. Gillis and K. A. Smith (J. Immunol., 120, 2027 (1978)) using IL-2 dependent mouse T cells (CTLL2).

*BCDF (B-cell differentiation factor)

By the method of Kishimoto et al. (J. Immunol., 127, 412 (1981) using CESS cell strain.

Next, the above fraction was chromatofocused using PBE94 (Pharmacia) gel. More specifically, the above fraction was fractionated using 0.025M imidazolehydrochloric acid (pH 4) as a starting buffer and Polybuffer 74-hydrochloric acid (pH 4) as an eluent. When the resulting fractions were checked for GIF activity, this activity was found to be present in the region of isoelectric points (PI) of 6.4 to 6.6.

Figure 2:
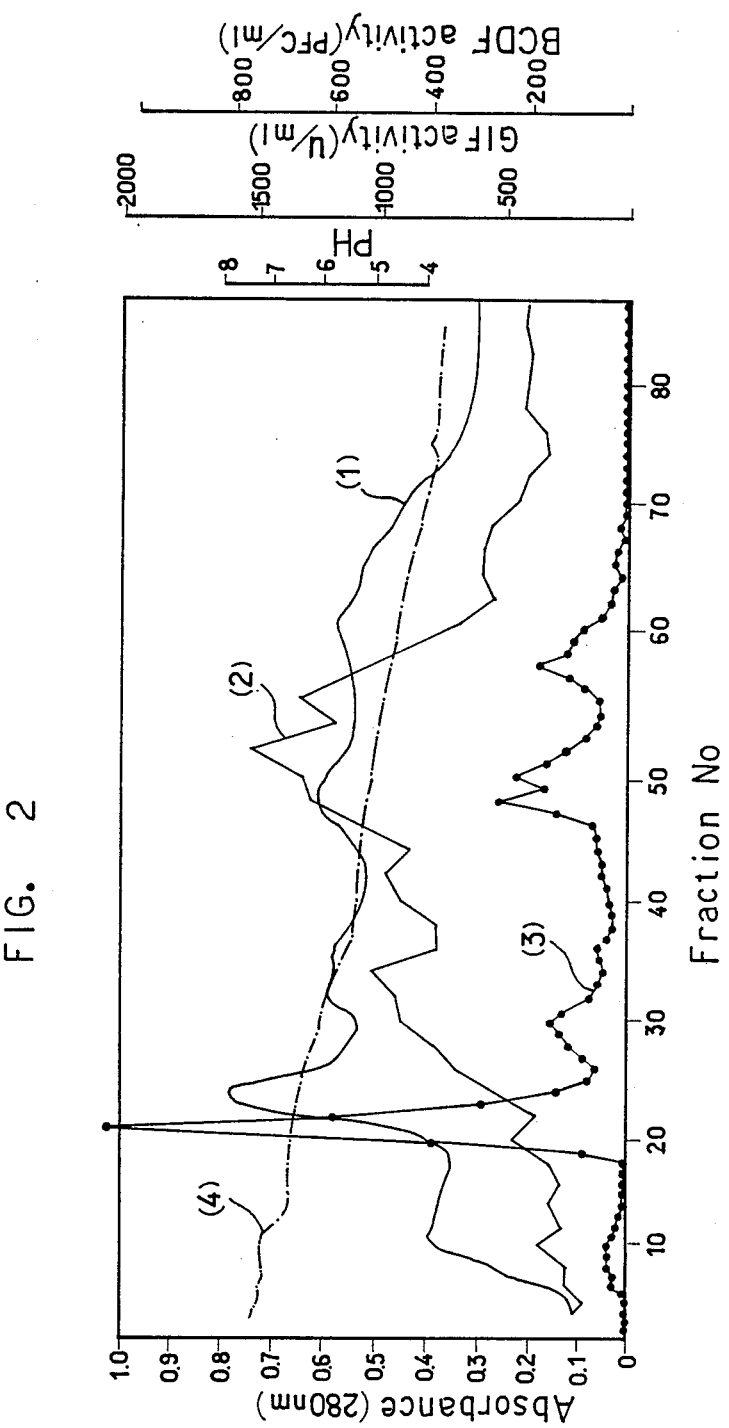
FIG. 2 shows chromatofocusing results.

FIG. 2 shows the results of chromatofocusing. In the diagram, the fraction number is plotted as abscissa. Plotted as ordinate are the absorbance with $OD_{280}$ (represented by curve (1)), BCDF activity (curve (2)), GIF activity of the invention (curve (3)) and pH (curve (4)).

The GIF-active fraction was further subjected to reverse-phase high-performance liquid chromatography ($C_4$ Highpore reverse-phase column (RP304), product of BioRad, 250 mm$\times$4.6 mm (diam.), mobile phase: A liquid=0.1% TFA and B liquid=0.1% TDFA+70% acetonitrile, concentration gradient: change from 100% A liquid to 100% B liquid over a period of 80 min, flow rate: 1 ml/min) to obtain a fraction of 44$\pm$3% acetonitrile. This fraction exhibited no IL-2 activity. GIF activity did not agree with LAF activity.

Figure 3:
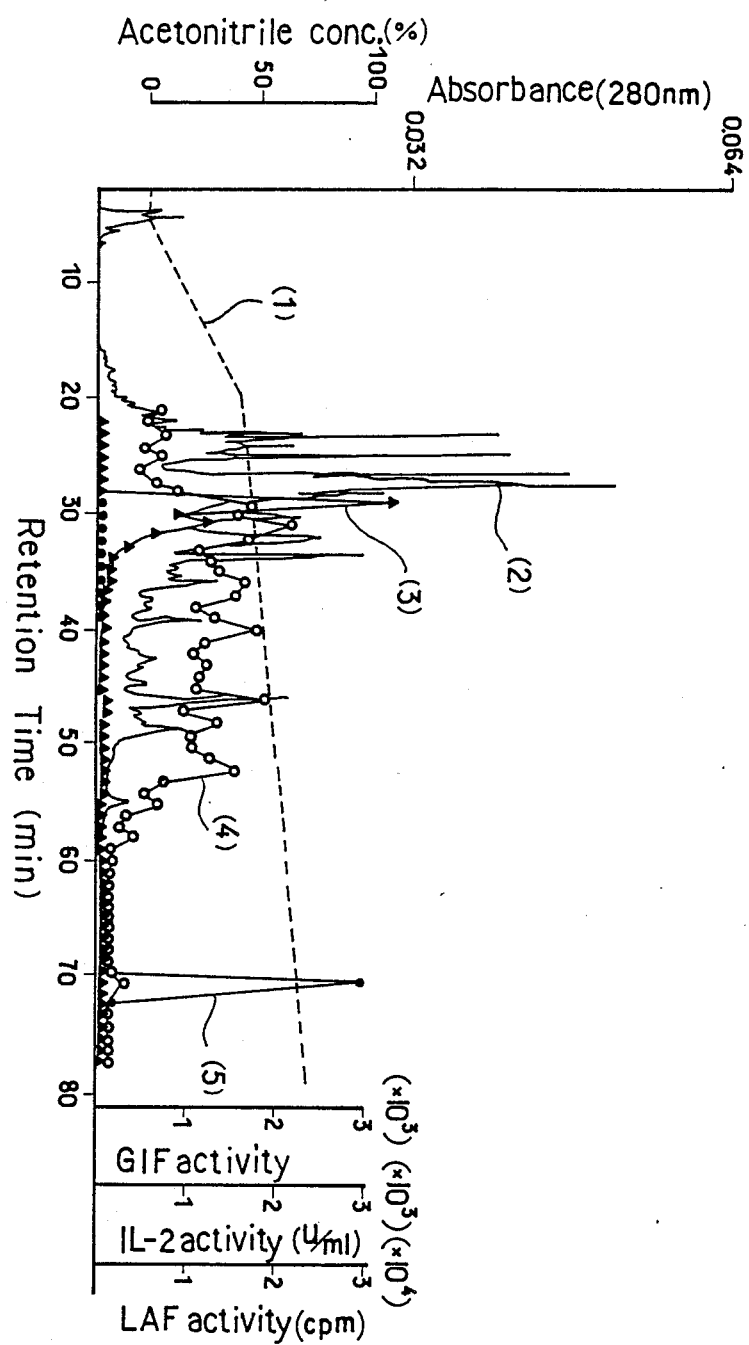
FIG. 3 shows the results of chromatographic analysis.

FIG. 3 shows the results of the chromatographic analysis. In the diagram, the retention time is plotted as abscissa. Plotted as ordinate are the acetonitrile concentration represented by curve (1), absorbance of protein (OD 280) at 280 nm represented by curve (2), GIF activity of the invention represented by curve (3), LAF activity represented by curve (4) and IL-2 activity represented by curve (5).

Thus, the natural type GIF of the present invention was isolated.

(II) Preparation of Natural Type GIF

Human peripheral blood lymphocytes were added to RPMI-1640 medium containing 1% FCS, 0.1 μg/ml of indomethacine, 20 mM of N-2-hydroxyethylpiperazine-N'-2-ethanesulfonic acid (HEPES) and 10 μg/ml of LPS (Difco) to prepare a cell suspension having a concentration of $1 \times 10^6$ cells/ml.

The suspension was incubated in a $CO_2$ incubator (NAPCO 5300, Napco Co., Ltd.) at 37° C. for 20 to 24 hours, the culture was centrifuged (10000 r.p.m.×30 min) to obtain 24300 ml of supernatant, and the supernatant was concentrated to 10 times the concentration using pericon membrane (molecular weight cut-off 10000, product of Millipore). The concentrate obtained will hereinafter be referred to as "starting liquid".

The starting liquid was fractionated by the ammonium sulfate precipitation method as in the procedure (I) with ice cooling. Fractions with an ammonium sulfate concentration of 50 to 80% were found to contain a GIF-active precipitate. The precipitate was dissolved in saline and then dialyzed with saline.

The resulting ammonium sulfate fraction was divided into four portions, and each portion was subjected to gel chromatography at 4° C. using Ultragel AcA54 (LKB) under the following conditions.

Column: 88 cm×4.4 cm (diam.)
Eluent: Phosphate buffer saline (PBS) containing 0.02% polyethylene glycol (molecular weight 6000) and 0.02% $NaN_3$
Flow rate: 30 ml/hour
Fraction volume: 15/ml/30 min/tube With each portion, fractions (No. 57 to No. 65) with a molecular weight of about 10,000 to 25,000 had GIF activity, and the active fractions were collected.

The combined fraction was then concentrated with ice-cooling using YM-5 membrane (Amicon) using 50 mM sodium acetate (pH 5.5) as a solvent. The concentrate was filtered with Milex GV (0.22 μm, product of Millipore).

The concentrate specimen obtained was divided into two portions, and each portion was subjected to ion-exchange chromatography (CM-HPLC) using Gilson high permeation liquid chromatography system under the following conditions.

Column: IEX-535CM (6.0×150 mm, Toyo Soda Mfg. Co., Ltd.)
Eluent A: 50 mM sodium acetate (pH 5.5)
Eluent B: 50 mM sodium acetate (pH 5.5) containing 0.5M NaCl
Flow rate: 0.5 ml/min.

| Fraction volume: | Retention time: |
|---|---|
| 0–60 min | 2 ml/4 min/tube |
| 60–120 min | 0.5 ml/min/tube |
| 120–180 min | 2 ml/4 min/tube |

Concentration gradient:

| Time (min) | % B |
|---|---|
| 0 | 0 |
| 40 | 0 |
| 120 | 20 |
| 140 | 100 |
| 165 | 100 |
| 170 | 0 |

The CM-HPLC procedure resulted in a GIF active fraction with a retention time of 90 to 91 minutes.

The active fraction (No. 45) was then subjected to reverse-phase high-performance liquid chromatography under the following conditions.

Column: $C_4$ Highpore reverse-phase column (RP304, Bio-Rad, 250 mm×4.6 mm (diam.))
Eluents:
A liquid=0.1% TFA
B liquid=acetonitrile-1% TFA (9:1)
Flow rate: 1 ml/min.

| Flow rate: | 1 ml/min. | |
|---|---|---|
| Chart speed: | Retention time: | |
| | 0–50 min | 5 min/cm |
| | 50–80 min | 2 min/cm |

Concentration gradient:

| Time (min) | % B |
|---|---|
| 0 | 0 |
| 5 | 0 |
| 15 | 20 |
| 75 | 45 |
| 80 | 100 |
| 85 | 100 |
| 90 | 0 |

Fraction volume: 2 ml/2 min/tube

Figure 4:
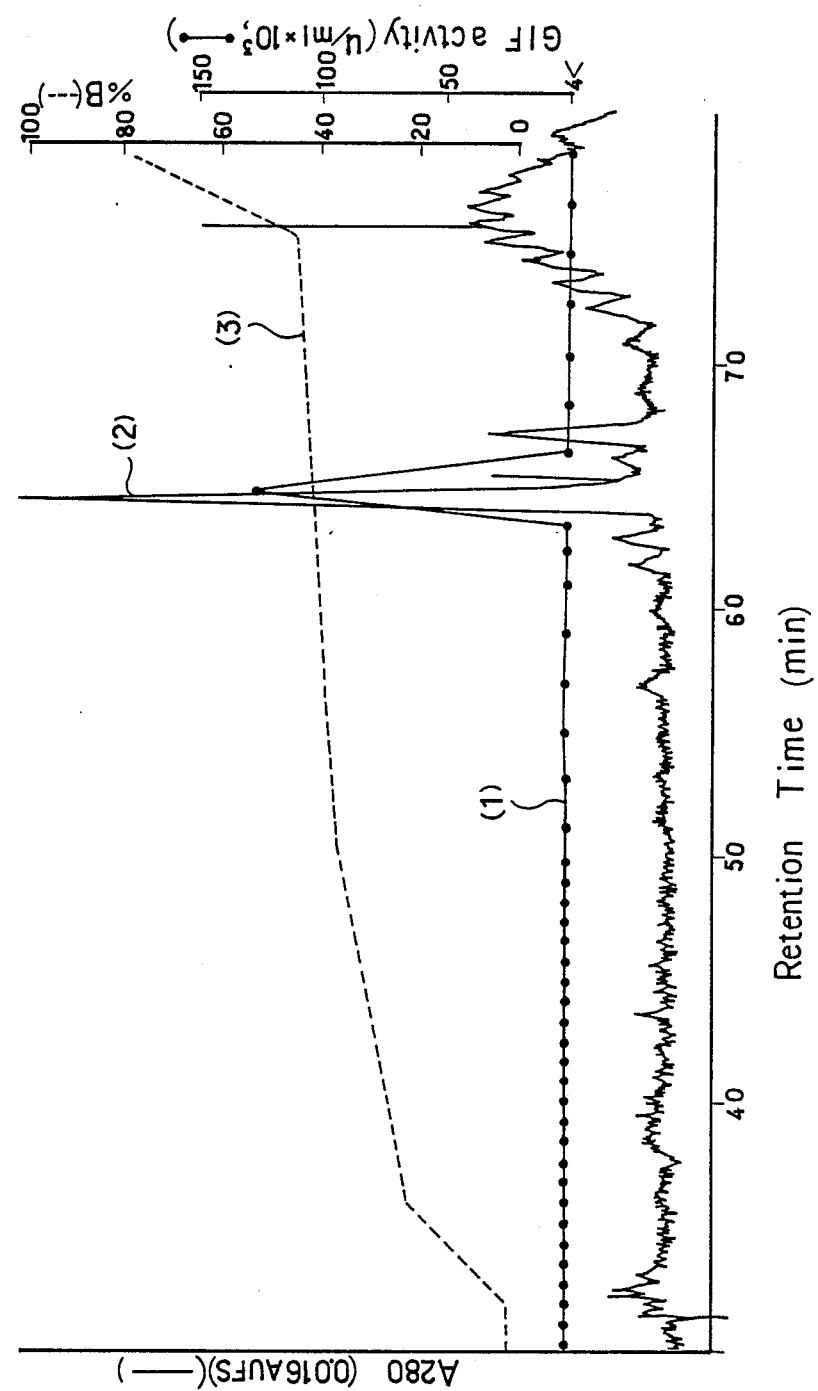
FIG. 4 shows chromatography results.

FIG. 4 shows the results of the chromatography. In diagram, plotted as abscissa is the retention time (min), and plotted as ordinate are the GIF activity (curve 1), protein absorbance ($A_{280}$, curve 2) at 280 nm and concentration gradient (%B, curve 3) of the eluate.

A fraction with a retention time of 63.9 to 65.3 minutes exhibited a single protein absorbance peak matching that of GIF.

The specific activity was $2.1 \times 10^7$ units/mg protein.

SDS polyacrylamide gel electrophoresis (SDS-PAGE)

The GIF obtained by the procedure (II) was subjected to SDS-PAGE by the method of Laemmli, U.K. (Nature, 277, 680 (1970)) under the following conditions.

Specimen: A 10 μl quantity of the GIF-active fraction was completely dried, then dissolved in Laemmli sample buffer (containing 2-mercapto ethanol in an amount of 1/20 the volume of the buffer) and treated at 100° C. for 4 minutes.

Gel: 15% Polyacrylamide gel 0.75 mm in thickness
Apparatus: PROTEAN, product of Bio-Rad
Electrophoresis: 20 mA constant current for 2 hours The gel resulting from the electrophoresis was dyed with Silver Stain Kit (Bio-Rad) with the results shown in FIG. 5.

Figure 5:
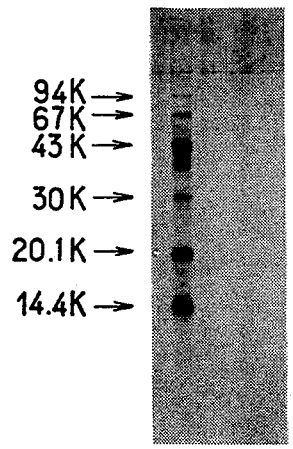
FIG. 5 and FIG. 6 show electrophoresis results.

With reference to FIG. 5, lane (1) resulted from the following molecular weight markers, lane (2) from the GIF specimen, and lane (3) from 10 μl of 0.1% TFA used in place of the GIF-active fraction and treated in the same manner as the specimen. Molecular weight markers for lane (1)

- 94K: Phosphorylase b
- 67K: Albumin
- 43K: Ovalbumin
- 30K: Carbonic anhydrase
- 20.1K: Trypsin inhibitor
- 14.4K: α-Lactoalubumin FIG. 5 shows that GIF is electrophoresed as a single band at a molecular weight of about 18K.

Isoelectroforcussing (IEF)

The GIF obtained by the procedure (II) was subjected to IEF using amphorine PAG plate (LKB) 3.5 to 9.5 in pH range and Model 1415 (Bio-Rad) under the following conditions.

Specimen: A 10 μl quantity of the GIF-active fraction as diluted fivefold with 25 mM sodium phosphate buffer (pH 7.4).

| Electrode solutions | Anode solution = 1 M H₃PO₄ Cathode solution = 1 M NaOH |
|---|---|
| Electrophoresis | With constant power of 1 W/cm gel width with cooling (10° C.) for 90 minutes |

Staining: With silver stain Kit

Figure 6:
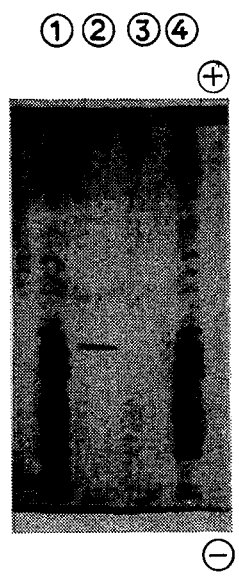

FIG. 6 shows the results of the electrophoresis. With reference to the drawing, lanes (1) and (4) resulted from 20 μl molecular weight marker, lane (2) from 50 μl of the GIF specimen, and lane (3) from 50 μl of a dilution prepared from 10 μl of 0.1% TFA in the same manner as the specimen with use of the buffer.

The gel resulting from the electrophoresis was sliced at a spacing of 5 mm or 2 mm, subjected to extraction with use of 1 ml of 10% FCS-added RPMI 1640 with shaking (for two days) and then checked for GIF cativity. The isoelectric point was calculated from the pH measurement after the electrophoresis.

Figure 7:
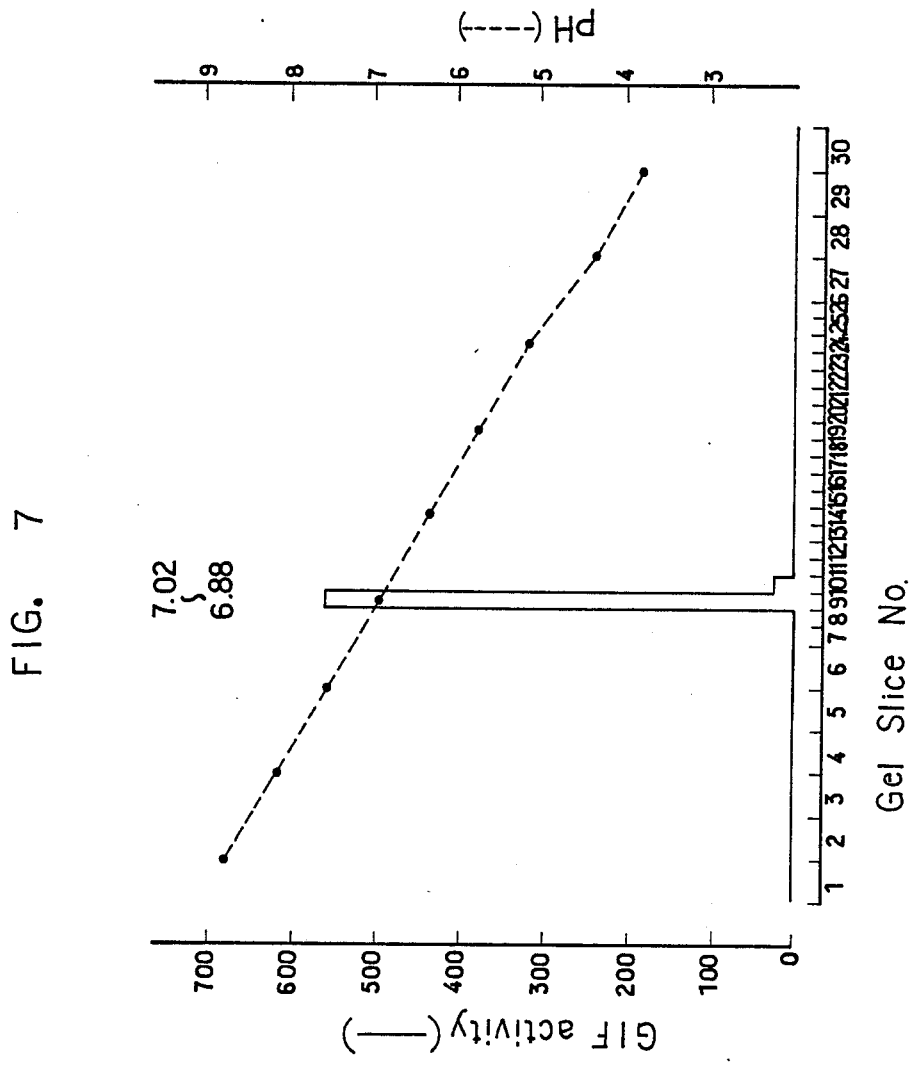
FIG. 7 shows isoelectric point calculated after electrophoresis.

FIG. 7 shows the results. With reference to FIG. 7, the gel slice number is plotted as abscissa, vs. the pH gradient (represented by broken line) and GIF activity (solid line) as ordinate.

FIGS. 6 and 7 reveal that the GIF has an isoelectric point (PI) of 7.02 to 6.88 and appears as a single band at this position.

Amino acid composition ratio

The GIF obtained by the procedure (II) was hydrolyzed (with 4N methanesulfonic acid for 24 hours) and then analyzed by the o-phthalaldehyde (OPA) method using an amino acid analyzer (Hitachi Ltd.).

The analysis revealed that the GIF contains the following amino acids in the mole ratio given below based on Phe.

Under the above analysis conditions, Pro and Cys can not be determined. Further it is known that Ser and Thr decomposes generally about 5 to about 10% under the above conditions.

| Amino acid | |
|---|---|
| Asp and/or Asn | 17.6 |
| Ser | 12.1 |
| Thr | 5.7 |
| Glu and/or Gln | 23.1 |
| Gly | 8.1 |
| Ala | 5.2 |
| Val | 11.8 |
| Met | 5.6 |
| Ile | 4.8 |
| Leu | 15.4 |
| Tyr | 3.9 |
| Phe | (9) |
| Lys | 15.3 |
| His | 1.1 |
| Trp | 0.8 |
| Arg | 3.0 |

Amino acid sequence

The N-terminal amino acid sequence of the GIF obtained by the procedure (II) was determined by a gas-phase sequencer (Applied Bio System).

Consequently, the GIF was found to have the following sequence of 20 amino acids at the N terminal.

Ala—Pro—Val—Arg—Ser—Leu—Asn—
Cys—Thr—Leu—Arg—Asp—Ser—Gln—
Gln—Lys—Ser—Leu—Val—Met

The eighth amino acid from the N terminal was estimated to be Cys since it was not detected as PTH amino acid.

Physiological activity

The GIF obtained by the procedure (II) was tested for physiological activities, with the result that none of TNF, INF, CSF, IL-2 and BCDF activities were found. This indicates that the GIF distinctively differs from substances having such physiological activities. GIF was also found to be extremely homogeneous.

Affinity tests for lectin columns

To check the GIF's obtained by the procedures (I) and (II) for sugar chain specificity, the properties of these substances to bond to lectin columns were determined by affinity chromatography with use of the lectins given below, under the following conditions.

Specimen: 3624 units/0.06 mg/0.5 ml
Gel volume: 1 ml
Washing solution: PBS⁻-0.005% PEG (or 0.05M tris-0.15M NaCl, pH 8.7 for SJA)
Eluent: Solution of the sugar of Table 1 in the washing solution Table 1 shows the results. The lectins were purchased from E.Y. Laboratories.

TABLE 1

| Lection | |
|---|---|
| ConA | Concanavalin A |
| WGA | Wheat Germ Agglutinin |
| UEA - I | Ulex europeus Agglutinin |
| DBA | Dolichos biflorus Agglutinin |
| WFA | Wistaria floribunda Agglutinin |
| PNA | Peanut Agglutinin |
| SBA | Soybean Agglutinin |
| SJA | Sophora japonica Agglutinin |

| Lectin | Eluent |
|---|---|
| ConA | 0.1 M α-Methylmannopyranoside |
| WGA | 0.2 M N—Acetylglucosamine |
| UEA - I | 0.05 M Fucose |
| DBA | 0.1 M N—acetylgalactosamine |
| WFA | Same |

TABLE 1-continued

| | |
|---|---|
| PNA | 0.2 M Galactose |
| SBA | Same |
| SJA | Same |

| Lectin | Sugar recognized |
|---|---|
| ConA | α-Man > α-Glc |
| WGA | GlcNAc β1-4GLcNAc |
| UEA - I | Same |
| DBA | α-GalNAc |
| WFA | Same |
| PNA | β-Gal |
| SBA | α-GalNAc > β-GalNAc |
| SJA | β-GalNAc > β-Gal |

Figure 8:
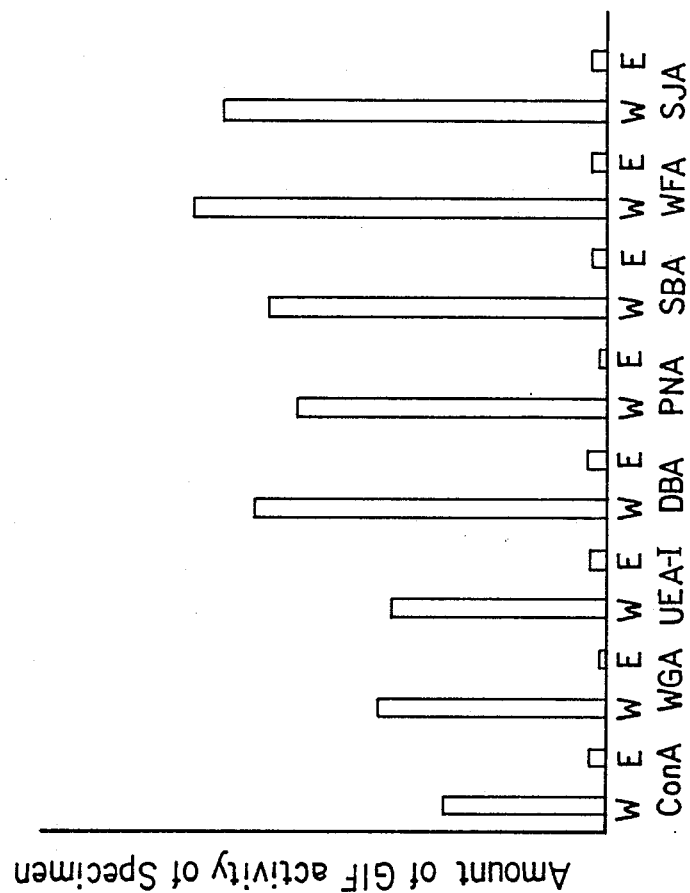
FIG. 8 shows GIF activity results and FIG. 9 also shown GIF activity results.

The results achieved by the GIF obtained by the procedure (I) are shown in FIG. 8. Plotted as ordinate in the diagram are the amount of activity contained in the fraction (W) passing through each lectin column without being adsorbed thereby, and the amount of activity contained in the fraction (E) adsorbed by the column and dissolved out by the eluent, the amounts of activity being in ratio relative to the GIF activity of the specimen which is taken as 100%. The fractions (W and E) from the columns are plotted as abscissa.

FIG. 8 shows the GIF has no affinity for any of the lectins. This indicates that these common sugar chains are not bonded to the GIF.

· The GIF obtained by the procedure (II) produced the same results as shown in FIG. 8.

Stability

The GIF's obtained by the procedures (I) and (II) were tested for stabilities as described below. The two substances were similar in the results achieved.

a. Temperature stability

The GIF was treated under the conditions given in Table 2 and checked for stability to temperature. The gel filtration fraction (3503 units/ml) was incubated at the listed temperature and thereafter checked for remaining activity (%) relative to the control group. Table 2 also shows the results.

TABLE 2

| Treating conditions | Remaining activity (%) |
|---|---|
| 37° C., 1 hr. | 97 |
| 56° C., 30 min. | 0 |
| 70° C., 30 min. | 0 |
| 80° C., 30 min. | 0 |
| 4° C., 1 hr. | 100 (Control) | b. pH stability

The GIF was treated similarly under the conditions given in Table 3 (at constant temperature of 4° C.) and then checked for stability to pH similarly. Table 3 also shows the results.

TABLE 3

| Treating conditions | Remaining activity (%) |
|---|---|
| pH 7.4, 5 hr. | 100 (Control) |
| pH 2.0, 5 hr. | 60 |
| pH 4.0, 5 hr. | 80 |
| pH 6.0, 5 hr. | 90 |
| pH 8.0, 5 hr. | 95 |
| pH 9.5, 5 hr. | 75 | c. Stability to proteases

In the same manner as above a., the GIF was checked for stability to proteases under the conditions given in Table 4 below. Trypsin Type III (12700 BAEE units/mg protein, product of Sigma) was used at a concentration of 1 mg/ml as trypsin. The pronase (45000 p.u.k/g protein) produced by Kaken Kagaku Co., Ltd. was used at a concentration of 1 mg/ml as pronase.

TABLE 4

| Treating conditions | Remaining activity (%) |
|---|---|
| With phosphate buffered saline (pH 7.4) at 37° C. for 2 hours | 100 (Control) |
| With trypsin at 37° C. for 2 hours | 0 |
| With pronase at 37° C. for 2 hours | 0 |

Table 4 indicates that the GIF is inactivated when treated with trypsin as well as with pronase.

Figure 9:
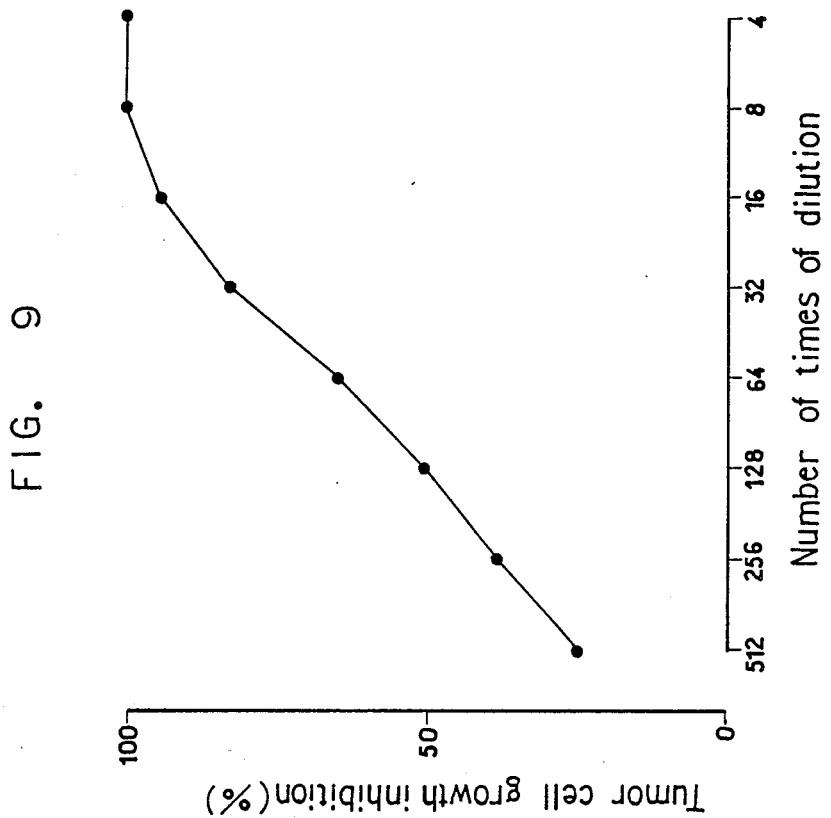

Dose-response curve of GIF activity (a) The GIF specimen (144.6 units/ml, 723 ng/ml in protein concentration) obtained by the procedure (I) was used for determining dose-response curve of GIF activity at varying times of dilution. FIG. 9 shows the results. In the diagram, the number of times of dilution is plotted as abscissa, and the percent tumor cell growth inhibition (GIF activity) as the ordinate.

FIG. 9 shows that the GIF achieves about 50% activity at a dose of several tens of ng/ml.

(b) The antitumor activity of the natural type GIF obtained by the procedure (II) on various cancer cells was determined by the following colony inhibition test and growth inhibition test.

Colony inhibition test

Into the wells of 12-well tissue culture plate (product of Coster) was placed a suspension of test cancer cells in 10% FCS containing RPMI 1640 at a concentration of $2 \times 10^2$ to $5 \times 10^2$ cells/well (500 μl/well).

The GIF specimen was placed into each well to a final concentration of 1.6 to 1000 units/ml. Further a control was prepared without using any GIF specimen.

The suspension was incubated in the presence of 5% carbon dioxide gas for 1 week. The medium was thereafter removed by an aspirator, each well was washed with PBS containing $CaCl_2$ (PBS+) twice, and the resulting colonies were fixed with 100% methanol, dyed by giemsa staining and then counted.

Percent colony inhibition was calculated from the following equation.

Colony inhibition (%)=

$$\left(1 - \frac{\text{Number of colonies in specimen}}{\text{Number of colonies in control}}\right) \times 100$$

Figure 10:
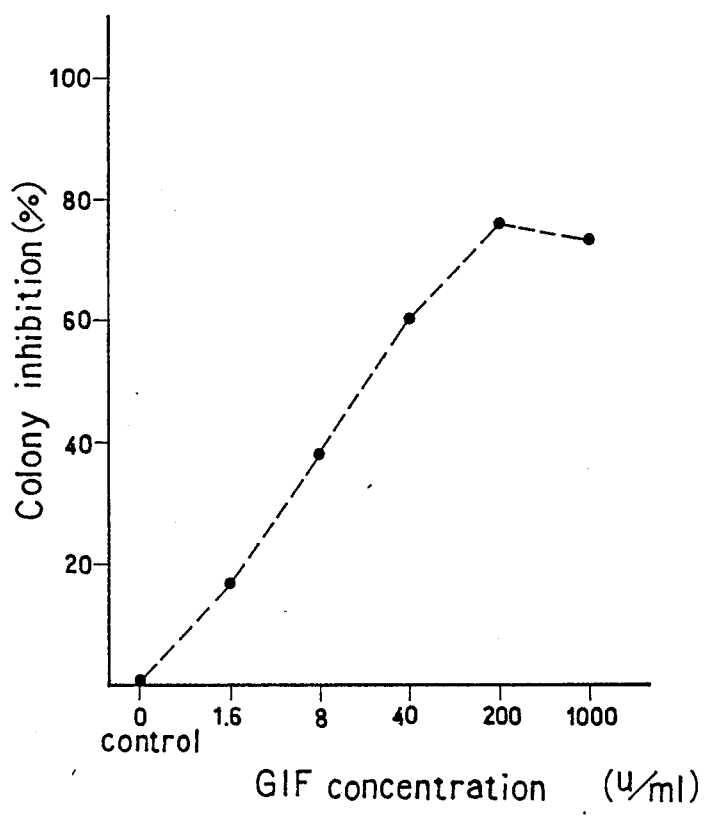
FIG. 10 shows results achieved with the use of a human lung cancer cell line A-549.

FIG. 10 shows the results achieved with use of A-549 (human lung cancer cells, ATCC CCL185). In the drawing, the GIF concentration (units/ml) is plotted as abscissa vs. the percent colony inhibition as ordinate.

Growth inhibition test

Into the wells of 96-well tissue culture plate (product of Corning) was placed a suspension of test cancer cells in 10% FCS containing RPMI 1640 at a concentration of $2 \times 10^3$ to $5 \times 10^3$ cells/well (100 μl/well).

The GIF specimen was placed into each well in an amount of 100 μl at a final concentration of 1 to 10000 units/ml medium. A control was prepared without using any GIF specimen.

The cells were incubated at 37° C. in the presence of 5% carbon dioxide gas for 4 to 5 days, 50 μl of 0.05% Neutral Red was thereafter added to each well, and the cells were further incubated at 37° C. in the presence of 5% carbon dioxide gas for 1 hour. Each well was then washed with PBS not containing $CaCl_2$ (PBS−), 100 μl of a pigment extraction buffer was placed into the well, and the absorbance (O.D.) of the well was measured at 540 nm.

Percent growth inhibition was calculated from the following equation.

$$\text{Percent growth inhibition} = \left(1 - \frac{O.D.\ of\ specimen}{O.D.\ of\ control}\right) \times 100$$

Figure 11:
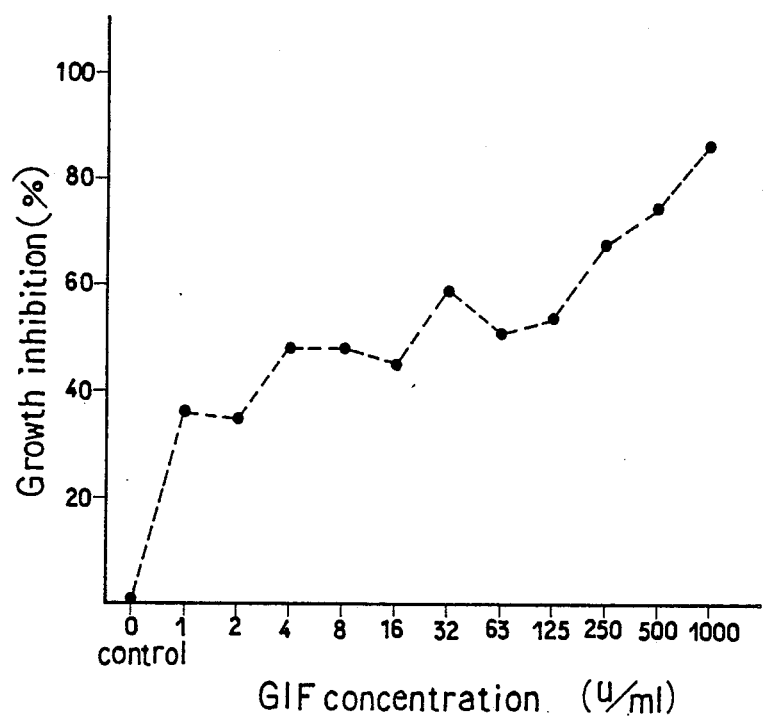
FIG. 11 shows the results achieved with a human renal adenocarcinoma cell line and FIG. 12 shows the results achieved with a human breast adenocarcinoma cell line.
Figure 12:
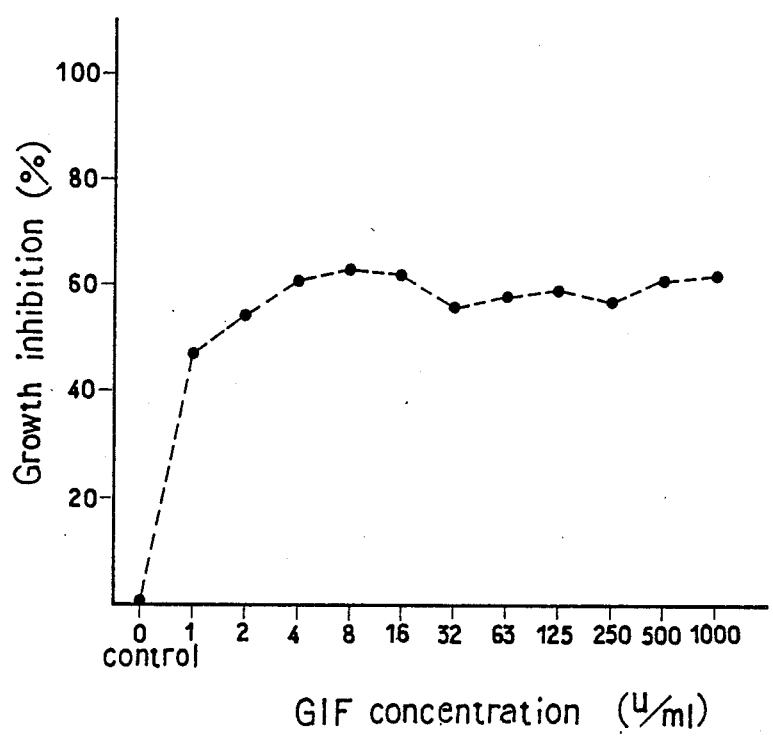

The results achieved by ACHN (human renal adenocarcinoma, ATCC CRL1611) are shown in FIG. 11, and those achieved by SK-BR-3 (human breast adenocarcinoma, ATCC HTB30) are shown in FIG. 12. In these diagrams, the GIF concentration (units/ml) is plotted as abscissa vs. the percent growth inhibition as ordinate.

Determination of primary structure of GIF protein (1) Human peripheral blood was collected, from which $1.9 \times 10^{10}$ lymphocytes were obtained by the Ficoll-Hypaque density gradient centrifugation method (Eur. J. Immunol. 4, 808 (1974)), A quantity of the lymphocytes were suspended in RPMI 1640 medium containing 5% of human serum at a concentration of $4 \times 10^8$ cells/ml. The suspension was dividedly placed into Petri dishes, 9 cm in diameter, and the cells were incubated in the presence of 5% carbon dioxide gas at 37° C. for one hour. The cells which were not adhered on the bottom of each dish were removed, and were stimulated with RPMI 1640 medium containing 10% FCS, 0.5 ng/ml of TPA (product of Sigma) and 10 μg/ml of LPS (product of Difco). After incubating the cells in 5% carbon dioxide gas at 37° C. for 4 hours, $9 \times 10^8$ adhered lymphocytes were obtained using PBS and 0.02% EDTA.

The cells adhered on the bottoms of the dishes were stimulated with 10 μg/ml of LPS under the same incubation conditions as above. The supernatant of the culture was thereafter checked for GIF activity at a time interval.

Figure 13:
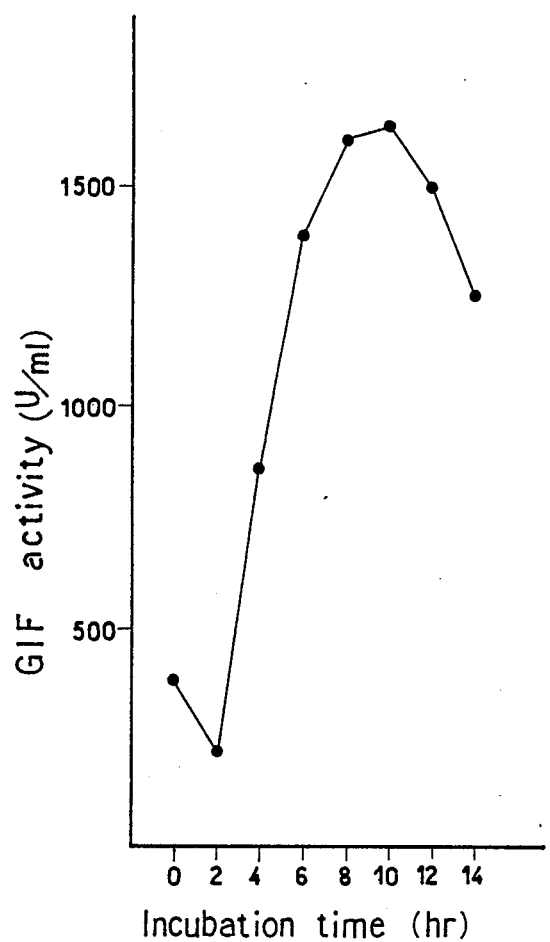
FIG. 13 shows GIF activity in relation to incubation time as to a culture supernatant.

FIG. 13 shows the results. In the diagram, the incubation time (hours) is plotted as abscissa vs. the GIF activity (units/ml) as ordinate.

FIG. 13 indicates that the culture supernatant started to exhibit the GIF activity 4 hours after the stimulation with LPS and that mRNA producing GIF protein can be prepared from human adhered cells obtained 4 hours after the stimulation.

(2) Human adhered lymphocytes ($9 \times 10^8$ cells) induced over a period of 4 hours with 0.5 ng/ml of TPA and 10 μg/ml of LPS by the procedure (1) were dissolved in 30 ml of 6M guanidine thiocyanate solution (6M guanidine isothiocyanate, 5 mM citrate (pH 7.0), 0.1M 2-mercarpto ethanol and 0.5% Sarkosyl), and the DNA was thereafter sheared with a 50-ml syringe barrel having G18G injection needle. A 12 g quantity of cesium chloride (CsCl) was completely dissolved in the solution. Portions (6.4 ml each) of the solution were superposed on 4 ml of 5.7M CsCl (5.7M CsCl-0.1M EDTA), and the combined layer was centrifuged by Beckman SW-40 Ti rotor at 31500 r.p.m. and 25° C. for 20 hours. The RNA pellet sediment was washed with 70% ethanol and dissolved in TE solution (10 mM tris-HCL (pH 7.5), 1 mM EDTA). To the solution were added 3M sodium acetate (pH 5.2) and ethanol in amounts of 1/9 and 2.2 times the amount of the solution, respectively, and the mixture was allowed to stand at −70° C. for one hour. The mixture was then centrifuged at 15000 r.p.m. and 4° C. for 20 minutes to collect the RNA, which was then dissolved in TE solution.

In this way, 250 μg of total RNA was prepared from about $9 \times 10^8$ adhered lymphocytes.

To obtain mRNA from the RNA, the RNA was subjected to column chromatography using oligo(dT) cellulose (Collaborative Resaerch Inc.). For adsorption, a solution of 10 mM tris-HCl (pH 7.5), 0.5M NaCl and 1 mM EDTA was used, and the column was washed with the same solution. The RNA was eluted with 10 mM tris-HCl (pH 7.5) and 1 mM EDTA.

Consequently 17.5 μg of mRNA was obtained.

(3) From the mRNA obtained by the procedure (2), cDNA was synthesized in vitro, and recombinant DNA was prepared using Okayama-Berg plasmid vector (Okayama, H. and Berg, P., Mol. Cell. Biol., 2, 161 (1982)) and was transformed in E. coli to obtain cDNA library. The procedures given below were followed.

(3-1) Preparation of vector primer and linker DNA

DNA (400 μg) of pBR322-SV40 (0.71–0.86) was digested with 700 units of KpnI (NEB) at 37° C. for 5 hours. The reaction was terminated with a mixture of 40 μl of 0.25M EDTA (pH 8.0) and 20 μl of 10% SDS. The reaction mixture was subjected to extraction with the same volume of phenol-chloroform (1:1). DNA was precipitated using ethanol, followed by centrifugation and washing with 70% ethanol to cellect DNA. The DNA obtained was dissolved in 200 μl of mixture of 140 mM sodium cacodylate, 30 mM tris-HCl (pH 6.8), 1 mM $CoCl_2$, 0.1 mM DTT and 0.25 mM dTTP (containing 0.5 μCi of $\alpha$-$^{32}$P-dTTP). The solution was treated with 400 units of terminal transferase (TTase, PL) for 30 minutes to elongate the dT chain. The reaction was terminated with 20 μl of 0.25M EDTA and 10 μl of 10% SDS, followed by extraction with phenol-chloroform 4 times. DNA was collected by precipitation with ethanol. Consequently, the dT chain was lengthened by about 70 bases.

The DNA thus obtained was digested at 37° C. for 6 hours with 17 units of HpaI (NEB) and electrophoresed with agarose (low-melting agarose, BRL, 1%) to collect about 2.7 kb DNA fragment.

After the electrophoresis, the DNA was stained with 0.5 μg/ml of ethidium bromide, the agarose containing the approximately 2.7 kb fragment was cut out under UV irradiation, and to the agarose was added 5 times the volume of 20 mM tris-HCl (pH 8.0)-1 mM EDTA to dissolve the agarose at 65° C. over a period of 5 minutes, followed by extraction with phenol, then with phenol-chloroform (1:1) and thereafter with chloroform. The DNA was collected by precipitation with ethanol.

Subsequently, the vector primer DNA was purified by oligo(dA) cellulose column chromatography. The DNA was dissolved in 1 ml of 10 mM tris-HCl (pH 7.3)-1 mM EDTA-1M NaCl buffer. The solution was ice-cooled, then placed on the column equilibrated with the same buffer, which was thereafter washed with 1 ml of the same buffer and subsequently returned to room temperature. Elution then followed with 10 mM tris-HCl (pH 7.3)-1 mM EDTA to collect the peak fraction. The DNA was collected by precipitation with ethanol, then dissolved in 100 μl of 10 mM tris-HCl (pH 7.3)-1 mM EDTA and stored at 4° C.

Linker DNA was prepared by the following procedure. pBR322-SV40 (0.19-0.32) DNA (100 μg) was digested with 120 units of PstI (NEB) at 37° C. for 1.5 hours. The termination of the reaction was followed by extraction with phenol-chloroform and precipitation with ethanol. The DNA collected was dissolved in 50 µl of mixture of 140 mM sodium cacodylate, 30 mM tris-HCl (pH 6.8), 1 mM CoCl₂, 0.1 mM DTT and 0.25 mM dGTP (containing 1 µCi of α-³²P-dGTP). The solution was acted on by 60 units of TTAse for 20 minutes, whereby a dG chain of 18 bases was attached. After the termination of the reaction, the DNA was collected, digested with 50 units of HindIII (Takara Shuzo Co., Ltd.) and electrophoresed with agarose (1.8%) in the same manner as above to collect about 0.28 kb DNA fragment and obtain 2.3 µg of linker DNA.

(3-2) Synthesis of cDNA and preparation of cDNA library

RNA (5 µg) was dried in a vacuo, then dissolved in 10 µl of 5 mM tris-HCl (pH 8.3) heated at 65° C. for 5 minutes and immediately cooled to 37° C. To the reaction mixture was added 20 µl of mixture of 50 mM tris-HCl (pH 8.3), 8 mM MgCl₂, 30 mM KCl, 0.3 mM DTT, 2 mM dNTP and 10 µCi of α-³²P-dCTP. The resulting mixture was maintained at 37° C. for 5 minutes.

Then units of RTase (reverse transcriptase, product of Seikagaku Kogyo Co., Ltd.) was added to the mixture and reacted therewith at 37° C. for 15 minutes. With addition of 10 units of RTase again, the mixture was maintained at the same temperature for 15 minutes. The reaction was terminated with 2 µl of 0.25 mM EDTA (pH 8.0) and 1 µl of 10% SDS, followed by extraction with phenol-chloroform. To the extract were added 20 µl of 4M ammonium acetate and 80 µl of ethanol, and the mixture was frozen at −70° C. for 15 minutes, then thawed at room temperature and centrifuged at 15000 r.p.m. and 4° C. for 10 minutes. The sediment was dissolved in 20 µl of 10 mM tris-HCl (pH 7.3). To the solution was added 19 µl of 4M ammonium acetate and 80 µm of ethanol to reprecipitate.

The precipititate was collected, washed with 70% ethanol and dissolved in 15 µl of mixture of 30 mM tris-HCl (pH 6.8), 1 mM CoCl₂, 0.1 mM DTT, 0.2 µg of poly A and 66 µM of (α-³²P)dCTP) (10 µCi). TTase (P. L., 18 units) was added to the solution and reacted therewith at 37° C. for 5 minutes. The reaction mixture was rapidly cooled to 0° C., and the reaction was terminated with 1.3 µl of 0.25M EDTA and 0.65 µl of 10% SDS, followed by extraction with phenol-chloroform and precipitation with ethanol.

The precipitate was collected by centrifugation and then digested with 4 units of HindIII (Takara Shuzo Co., Ltd.) at 37° C. for 2 hours. Termination of the reaction was followed by extraction with phenol-chloroform and precipitation with ethanol. The precipitate was collected and dissolved in 10 µl of mixture of 10 mM tris-HCl (pH 7.3) and 1 mM EDTA. With addition of 3 µl of ethanol, the solution was preserved at −20° C.

One µl of the specimen thus obtained was maintained along with 5 ng of linker DNA in 10 µl of mixture of 10 mM tris-HCl (pH 7.5), 1 mM EDTA and 0.1M NaCl at 65° C. for 2 minutes and then at 42° C. for 30 minutes, and thereafter cooled to 0° C. To the mixture was added 90 µl of a mixture solution of 20 mM tris-HCl (pH 7.5), 4 mM MgCl₂, 10 mM (NH₄)₂SO₄, 0.1M KCl, 0.1 mM β-NAD, 50 µg/ml BSA-6 units/ml of E. coli DNA ligase, and then the combined solution was maintained at 12° C. overnight.

To the solution was added 0.5 µl of 10 mM dNTP, 0.56 µl of 10 mM NAD, 0.5 µl of E. coli DNA polymerase I (product of Boehringer Mannheim) and 0.2 µl of RNase H (PL). The mixture was maintained at 12° C. for one hour and then at 25° C. for one hour, and thereafter frozen at −20° C. for preservation.

E. coli HB101 strain was incubated to OD₅₅₀ of 0.45 in LB medium (10 g of bacto-trypton, 5 g of bacto-yeast extract and 10 g/liter of NaCl). The culture was ice-cooled for 5 minutes and then centrifuged at 4° C. at 8000 r.p.m. for 5 minutes to harvest the cells. The pellets of cells were suspended in an ice-cooled mixture of 30 mM potassium acetate, 100 mM RbCl, 10 mM CaCl₂, 50 mM MnCl and 15% glycerin, maintained at 0° C. for 5 minutes and centrifuged at 4° C. at 8000 r.p.m. for 5 minutes. The cells collected were suspended again in a mixture of 10 mM MOPS (morpholinopropanesulfonic acid), 75 mM CaCl₂, 10 mM RbCl and 15% glycerin and maintained at 0° C. for 15 minutes to prepare competent cells, which were thereafter preserved at −70° C.

The frozen suspension was thawed at room temperature. The DNA specimen (20 µl) was added to a 400 µl portion of the suspension, and the mixture was allowed to stand at 0° C. for 30 minutes, subjected to heat shock at 42° C. for 90 seconds and then allowed to stand again at 0° C. for 1 to 2 minutes. With addition of 2 ml of LB medium, the mixture was maintained at 37° C. for 30 minutes. LB medium (50 times the volume of the mixture) was inoculated with the mixture, followed by incubation at 37° C. for 6 hours. Ampicillin was added to the culture to a concentration of 50 µg/ml, followed by incubation again overnight, whereby cDNA library was prepared. The cDNA library was preserved in 50% glycerin at −20° C.

(3-3) Preparation of synthetic probe

The following nucleotide acid sequence was derived from the amino acid sequence (20 residues from the N terminal) of the native GIF determined as above.

| Ala | —Pro | —Val | —Arg | —Ser | —Leu | —Asn— |
|---|---|---|---|---|---|---|
| 5' GCC | CCC | GTG | AGG | TCC | CTG | AAC |
| 3' CGG | GGG | CAC | TCC | AGG | GAC | TTG |

| —Cys | —Thr | —Leu | —Arg | —Asp | —Ser | —Gln— |
|---|---|---|---|---|---|---|
| TGC | ACC | CTG | AGG | GAC | TCC | CAG |
| ACG | TGG | GAC | TCC | CTG | AGG | GTC |

| —Gln | —Lys | —Ser | —Leu | —Val | —Met | |
|---|---|---|---|---|---|---|
| CAG | AAG | TCC | CTG | GTG | ATG— | 3' |
| GTC | TTC | AGG | GAC | CAC | TAC— | 5' |

The above nucleotide sequence was determined according to the human codon usage frequency (Nucleic Acid Research, 9, r43–74 (1981)).

A nucleotide sequence (shown in the lowest line) complementary to the base sequence of the above formula is synthesized by the following method to use the complementary sequence as a probe for selecting a transformant having cDNA coding for GIF. Thus, the fully protected DNA was synthesized by the solid-phase phosphite triester method wherein N,N-dialkyl-methyl phosphoramidite derivative is used as a condensation unit (Nature, 310, 105 (1984)), using an automatic synthesizer (380A DNA Synthesizer, Applied Biosystems Inc., Foster City, Calif. 94404, U.S.A.). Subsequently, the fully protected DNA was treated with 28% aqueous ammonia at 55° C. for 10 hours, whereby the protective groups (i.e., the acyl groups for the amino groups of A, G and C) other than DMTr (dimethoxytrityl) group attached to the hydroxyl group at the 5' terminal were removed to obtain partially protected DNA. Next, the partially protected DNA was purified by reverse-phase HPLC using $C_{18}$ column and then treated with 80% acetic acid at room temperature for 10 minutes to remove DMTr group. The nucleotide thus obtained was purified by electrophoresis using 10% polyacrylamide gel containing 7M urea and by gel filtration using Bio-gel P-30 (Bio-Rad) to obtain the desired DNA (60 mer).

The DNA (6 μg) thus obtained was reacted with 12 units of T4 polynucleotide kinase (Takara Shuzo) at 37° C. for one hour in 50 μl of reaction mixture (50 mM tris-HCl (pH 7.6), 10 mM $MgCl_2$, 10 mM 2-mercapto ethanol, 0.2 mg/ml of fetal bovine thymus DNA and 50 μCi (α-$^{32}$P)-ATP) to label the 5' terminal of the DNA. To separate the labeled DNA from the unreacted $^{32}$P, the reaction mixture was subjected to column chromatography using Biogel P-30 (Bio-Rad). The fraction of the labeled DNA was precipitated with 3M sodium acetate in 1/9 of the volume of the fraction and ethanol in 2.5 times the volume thereof. The precipitate was collected by centrifugration, dissolved in 400 μl of mixture of 10 mM tris-HCl (pH 8.0) and 1 mM EDTA and preserved at −20° C.

The specific activity of the resulting probe was at least $10^7$ cpm/μg DNA.

(3-4) Screening of cDNA library

Twenty-four nitrocellulose filters (Millipore HAIFO 8250), 80 mm in diameter, were placed over LB agar medium containing 50 μg/ml of ampicillin, and the cDNA library solution was spread over the filters, as so diluted that 5000 colonies were applied to each filter, followed by incubation overnight at 37° C.

A fresh nitrocellulose filter was placed over the filter where colonies appeared to prepare a replica filter.

The original filter (master filter) was preserved at 4° C. The replica filter was held on the same agar medium as above at 37° C. for 6 hours for incubation and thereafter transferred onto LB agar medium containing 200 μg/ml of chloramphenicol, followed by incubation at 37° C. overnight.

The filter was treated with 0.5N NaOH, then with 1M tris-HCl (pH 8.0) and thereafter with a mixture of 1M tris-HCl (pH 8.0) and 1.5M NaCl. The filter was then dried in air and subsequently baked under a vacuum at 80° C. for 2 hours.

The baked filter, while being lightly shaken, was maintained at 68° C. overnight in 20 ml of solution of 1.2M NaCl, 0.12M trisodium citrate, 10 mg/ml of Ficoll, 10 mg/ml of polyvinylpyrrolidine, 10 mg/ml of BSA, 0.1% SDS and 1 mg/ml of salmon sperm DNA. The solution was replaced by a solution of 1.2M NaCl, 0.12M trisodium citrate, 10 mg/ml of Ficoll, 10 mg/ml of polyvinylpyrrolidine, 10 mg/ml of BSA, 0.1% SDS and $10^6$ cpm/ml of the probe, in which the filter was maintained at 42° C. overnight with light shaking for hybridization.

After the hybridization, the filter was withdrawn from the solution, washed with a solution of 1.2M NaCl, 0.12M sodium citrate and 0.1% SDS three times at room temperature and thereafter washed with the same solution at 60° C. until the count of the background of the filter became 200 cpm as determined by GM survey meter.

The filter was dried in air and then subjected to autoradiography at −70° C. for 2 days using sensitized paper and x-ray film (Fuji RX).

After developing the film, the colonies present in the signal region were scraped off from the master filter, and the foregoing procedure was repeated to isolate the colonies with a positive signal.

Consequently, clone I-2 having a strong signal was isolated.

(3-5) Analysis of clone

Restriction enzyme map of plasmid pGIF-α cDNA contained in clone I-2 was prepared.

Figure 14:
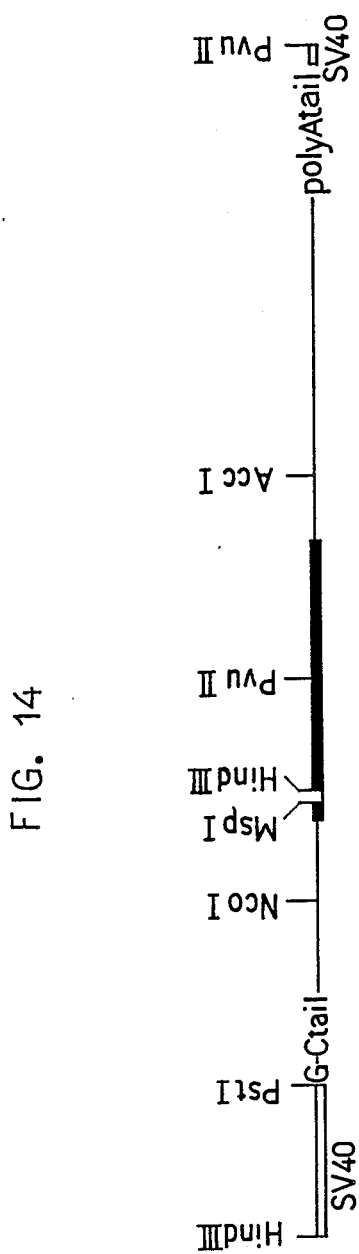
FIG. 14 shows a restriction enzyme map of plasmid pGIF-αcDNA of clone I-2.

FIG. 14 shows the map.

FIG. 14 reveals that the cDNA has sites to be cleaved with NcoI (Nippon Gene), Hind III (Nippon Gene), PvuII (Nippon Gene) and AccI (Nippon Gene), one site by each, these cleavage sites being arranged in this order from the 5' terminus. It was found that the cDNA has a length of about 1.5 kb which is sufficient to code for GIF having a molecular weight of about 18 K.

Next, the base sequence of pGIF-α cDNA was determined by the Maxam-Gilbert chemical modification method (Meth. Emzym. 65, 499–566, 1980) and the dideoxynucleotide chain termination method using M13 phage (Messing, J. and Vieira, J., Gene, 19, 269–276 (1982)).

CTTATTACAGTGGCAATGAGGATGACTTG

TTCTTTGAAGCTGATGGCCCTAAACAGATGAAG
                            Met Lys

TGCTCCTTCCAGGACCTGGACCTCTGCCCTCTG
Cys Ser Phe Gln Asp Leu Asp Leu Cys Pro Leu

GATGGCGGCATCCAGCTACGAATCTCCGACCAC
Asp Gly Gly Ile Gln Leu Arg Ile Ser Asp His

CACTACAGCAAGGGCTTCAGGCAGGCCGCGTCA
His Tyr Ser Lys Gly Phe Arg Gln Ala Ala Ser

GTTGTTGTGGCCATGGACAAGCTGAGGAAGATG
Val Val Val Ala Met Asp Lys Leu Arg Lys Met

CTGGTTCCCTGCCCACAGACCTTCCAGGAGAAT
Leu Val Pro Cys Pro Gln Thr Phe Gln Glu Asn

GACCTGAGCACCTTCTTTCCCTTCATCTTTGAA
Asp Leu Ser Thr Phe Phe Pro Phe Ile Phe Glu

GAAGAACCTATCTTCTTCGACACATGGGATAAC
Glu Glu Pro Ile Phe Phe Asp Thr Trp Asp Asn

GAGGCTTATGTGCACGATGCACCTGTACGATCa
Glu Ala Tyr Val His Asp Ala Pro Val Arg Ser

CTGAACTGCACGCTCCGGGACTCACAGCAAAAA
Leu Asn Cys Thr Leu Arg Asp Ser Gln Gln Lys

AGCTTGGTGATGTCTGGTCCATATGAACTGAAA
Ser Leu Val Met Ser Gly Pro Tyr Glu Leu Lys

GCTCTCCACCTCCAGGGACAGGATATGGAGCAA
Ala Leu His Leu Gln Gly Gln Asp Met Glu Gln

CAAGTGGTGTTCTCCATGTCCTTTGTACAAGGA
Gln Val Val Phe Ser Met Ser Phe Val Gln Gly

GAAGAAAGTAATGACAAAATACCTGTGGCCTTG
Glu Glu Ser Asn Asp Lys Ile Pro Val Ala Leu

GGCCTCAGGGAAAAGAATCTGTACCTGTCCTGC
Gly Leu Lys Glu Lys Asn Lue Tyr Leu Ser Cys

GTGTTGAAAGATGATAAGCCCACTCTACAGCTG
Val Leu Lys Asp Asp Lys Pro Thr Leu Gln Leu

```
GAGAGTGTAGATCCCAAAAATTACCCAAAGAAG
Glu Ser Val Asp Pro Lys Asn Tyr Pro Lys Lys

AAGATGGAAAAGCGATTTGTCTTCAACAAGATA
Lys Met Glu Lys Arg Phe Val Phe Asn Lys Ile

GAAATCAATAACAAGCTGGAATTTGAGTCTGCC
Glu Ile Asn Asn Lys Leu Glu Phe Glu Ser Ala

CAGTTCCCCAACTGGTACATCAGCACCTCTCAA
Gln Phe Pro Asn Trp Tyr Ile Ser Thr Ser Gln

GCAGAAAACATGCCCGTCTTCCTGGGAGGGACC
Ala Glu Asn Met Pro Val Phe Leu Gly Gly Thr

AAAGGCGGCCAGGATATAACTGACTTCACCATG
Lys Gly Gly Gln Asp Ile Thr Asp Phe Thr Met

CAATTTGTGTCTTCCTAAAGAGAGCTGTACCCA
Gln Phe Val Ser Ser

GAGAGTCCTGTGCTGAATGTGGACTCAATCCCT

AGGGCTGGCAGAAAGGGAACAGAAGGTTTTTGA

GTACGGCTATAGCCTGGACTTTCCTGTTGTCTA

CACCAATGCCCAACTGCCTGCCTTAGGGTAGTG

CTAAGACGATCTCCTGTCCATCAGCCAGGACAG

TCAGCTCTCTCCTTTCAGGGCCAATCCCAGCCC

TTTTGTTGAGCCAGGCCTCTCTCTCACCTCTCC

TACTCACTTAAAGCCCGCCYGACAGAAACCAGG

CCACATTTTGGTTCTAAGAAACCCTCCTCTGTC

ATTCGCTCCCACATTCTGATGAGCAACCGCTTC

CCTATTTATTTATTTATTTGTTTGTTTGTTTTG

ATTCATTGGTCTAATTTATTCAAAGGGGGCAAG

AAGTAGCAGTGTCTGTAAAAGAGCCTACTTTTT

ATTAGCTATGGAATCAATTCAATTTGGACTGGT

GTGCTCTCTTTAAATCAAGTCCTTTAATTAAGA

CTGAAAATATATAAGCTCAGATTATTTAAATGG

GAATATTTATAAATGAGCAAATATCATACTGTT

CAATGGTTCTCAAATAAACTTCACTAAAAAAAA

AAAAAAAAAAAAAAAAAAAAAA
```

The formula shows that the underlined region of the 312nd to the 317st nucleotides from the 5' terminal is complementary to the synthesized probe. The nucleotide sequence had 75% homology with the nucleotide sequence determined according to the human codon usage frequencies.

Further when the cDNA of pGIF was searched for the longest reading frame, this frame was found to be the region of the 57th to 771st nucleotides from the 5' terminal. The amino acid sequence corresponding to the nucleotide sequence of the 312nd to the 317st was found to be perfectly identical with the 20 amino acids at the N terminal of the natural type GIF. This indicates that the cDNA of pGIF-α is cDNA coding for a GIF precursor protein.

The above nucleotide sequence reveals that the natural type GIF is encoded in the nucleotide sequence of the 312nd to the 771st and is composed of 153 amino acids.

This result agreed with the foregoing properties of the natural type GIF (molecular weight, N-terminal amino acid sequence and amino acid composition).

Shown below in the primary structure of the protein of the natural type GIF thus determined.

| Ala | Pro | Val | Arg | Ser Leu | Asn Cys | Thr | Leu | Arg |
|---|---|---|---|---|---|---|---|---|
| Asp | Ser | Gln | Gln | Lys Ser | Leu Val | Met | Ser | Gly |
| Pro | Tyr | Glu | Leu | Lys Ala | Leu His | Leu | Gln | Gly |
| Gln | Asp | Met | Glu | Gln Gln | Val Val | Phe | Ser | Met |
| Ser | Phe | Val | Gln | Gly Gln | Glu Ser | Asn | Asp | Lys |
| Ile | Pro | Val | Ala | Leu Gly | Leu Lys | Glu | Lys | Asn |
| Leu | Tyr | Leu | Ser | Cys Val | Leu Lys | Asp | Asp | Lys |
| Pro | Thr | Leu | Gln | Leu Glu | Ser Val | Asp | Pro | Lys |
| Asn | Tyr | Pro | Lys | Lys Lys | Met Glu | Lys | Arg | Phe |
| Val | Phe | Asn | Lys | Ile Glu | Ile Asn | Asn | Lys | Leu |
| Glu | Phe | Glu | Ser | Ala Gln | Phe Pro | Asn | Trp | Tyr |
| Ile | Ser | Thr | Ser | Gln Ala | Glu Asn | Met | Pro | Val |
| Phe | Leu | Gly | Gly | Thr Lys | Gly Gly | Gln | Asp | Ile |
| Thr | Asp | Phe | Thr | Met Gln | Phe Val | Ser | Ser | |

EXAMPLE 2

(I) Preparation of Recombinant GIF (r-GIF)

Plasmid pGIF-α possessed by clone I-2 obtained by the procedure of Example 1, (II), (3-5) was cleaved with restriction enzymes HgiAI (NEB) and AccI (Nippon Gene) to obtain 581 base pairs (bp) gene coding for polypeptide I. The 5' terminal and 3' terminal of the gene were cut with nuclease mung bean (Pharmacia P-L Biochemicals). The fragment is inserted into M13 phage RFmp10 at SmaI site. E. coli JM 105 is infected with the phage and incubated to obtain single-strand (SS)-DNA.

Subsequently, in the presence of M13 Universal Primer and Deoxy NTPs (Takara Shuzo), DNA polymerase I (Klenow Fragment (Takara Shuzo) was caused to act on SS-DNA to synthesize double-strand (ds)-DNA, which was then cleaved with restriction enzymes EcoRI and BamHI (Nippon Gene) to obtain a DNA fragment having the desired restriction enzyme sites.

The fragment was inserted into expression vector pINIIIA-3 (Bio Technology, Vol. 2, 81-85 (1984)) at EcoRI and BamHI sites to obtain the desired plasmid pINIIIf-GIF-α.

FIG. 15 schematically shows the above procedure.

The vector plasmid obtained was inserted into E. coli HB101 for transformation to obtain the desired transformant.

The transformant was incubuated in L-broth medium (containing 50 μg of ampicillin per mil) with shaking at 37° C. When cells grew to $OD_{650}$ of 0.2, isopropyl-β-D-thiogalactopyranoside (IPTG) was added to the medium to a final concentration of 2 mM. One-ml samples of the culture were collected 2 hours, 5 hours and 6.5 hours after the addition of IPTG. Each sample was centrifuged (10000 r.p.m., five minutes), and the cells were collected, dissolved in 1 ml of EDTA-lysozymeTriton X100 (final concentration 1%), then sonicated and checked for GIF activity.

The above procedure was repeated using vector plasmid pINIIIA-3 as a control.

Table 5 shows the results.

TABLE 5

| DNA in E. coli transformant | Lapse of time after IPTG addition (hr) | GIF activity (units/ml culture) |
|---|---|---|
| pINIIIf-GIF-α | 2 | 12000 |
|  | 5 | 24200 |
|  | 6.5 | 40100 |
| pINIIIA-3 | 6.5 | not detected |

Table 5 shows that the desired GIF can be produced by incubating the transformant with plasmid pINIIIf-GIF-α.

(II) Preparation of r-GIF

The following oligodeoxynucleotides (I) and (II) were prepared by the procedures described below.

5'CGATAATGGCTCCTGTACGTTCTCT-GAACTGCACTCTC3'  (I)

5'CGGAGAGTGCAGTTCAGAGAACG-TACAGGAGCCATTAT3'  (II)

5'-0-Dimethoxytrityl and N-protected deoxynucleoside (Applied Biosystems Inc.) attached to macroporous silica were used as starting materials. The nucleotide chain was successively lenghtened from the 3' terminal toward the 5' terminal with the condensation units of 5'-0-dimethoxytrityl and N-protected deoxymononucleoside-3'-phosphoamidite, using an automatic synthesizer (380A DNA synthesizer, Applied Biosystems Inc.). The resulting product was treated with thiophenol for demethylation and further treated with 28% ammonia at room temperature to remove the nucleotide from the silica, whereby fully protected oligonucleotide was obtained. The above procedure was executed entirely by the automatic synthesizer (Hunkapiller et al., Nature, 310, 106 (1984)).

The oligonucleotide was treated with 2 ml of 28% aqueous ammonia at 55° C. for 10 hours to remove the N-protective group and obtain 5'-0-dimethoxytrityloligonucleotide. One fifth of the amount of the product was purified by reverse-phase high-performance liquid chromatography using ODS (Yamamura Kagaku Kenkyusho Co., Ltd.) column and then treated with 150 µl of 80% acetic acid at room temperature for 20 minutes to obtain crude oligonucleotide. The product was further purified by reverse-phase high-performance liquid chromatography with ODS column to obtain the desired oligonucleotide.

The plasmid pGIF-α obtained by the procedure of Example 1, (II), (3-5) was cleaved with restriction enzymes AccI and ClaI to obtain a DNA fragment of about 1.2 kilo base pairs (kbp), which was isolated and purified by agarose gel electrophoresis. The DNA fragment was made blunt at the ends cleaved with restriction enzymes AccI and ClaI, using DNA polymerase I (Klenow fragment).

On the other hand, BamHI linker (5' CGGATCCG 3') was phosphorylated at the 5' terminal with T4 polynucleotide kinase and joined to the blunt-ended DNA fragment with T4 DNA ligase, followed by digestion with restriction enzyme BamHI and further with restriction enzyme MspI. The resulting reaction product was electrophoresed on agarose gel to isolate purified MspI-BamHI DNA fragment of about 540 bp.

The oligodeoxynucleotides (I) and (II) synthesized above were phosphorylated at the 5' terminal with T4 polynucleotide kinase and joined to MspI-BamHI DNA fragment using T4 NDA ligase, followed by digestion with restriction enzymes BamHI and ClaI. The reaction product was electrophoresed on agarose gel to isolate purified ClaI-BamHI DNA fragment of about 580 bp.

On the other hand, plasmids pTMI (Fumio Imamoto, Metabolism, Vol. 22, 289 (1985)) were cleaved with restriction enzymes BamHI and ClaI, followed by agarose gel electrophoresis to isolate and purify DNA fragment of about 4.4 kbp having a trp promotor region. The DNA fragment and the ClaI-BamHI DNA fragment of about 580 bp prepared above were ligated with T4 DNA ligase to obtain the desired plasmid ptrpGIF-α.

The plasmid was introduced into E. coli HB101 for transformation, and the desired transformant E. coli HB101ptrpGIF-α was selected by the restriction enzyme analysis of the plasmid DNAs which was obtained by the boiling method (T. Maniatis, E. F. Fritsch and J. Sambrook, Molecular Cloning, p. 366, Cold Spring Harfor Laboratory, (1982)).

FIG. 16 schematically shows the above procedure.

The transformant prepared by introducing the plasmid ptrpGIF-α into E. coli χ1776 has been deposited under the name of Escherichia coli χ1776/ptrpGIF-α and deposition number FERM BP-949 in Fermentation Research Institute, Agency of Industrial Science and Technology since Dec. 12, 1985.

The transformant obtained above, i.e., E. coli HB101/ptrpGIF-α was incubated overnight at 37° C. with shaking in 10 ml of LB medium (1% trypsin, 0.5% yeast extract and 0.5% NaCl) containing 50 µg/ml of ampicillin and 20 µg/ml of L-tryptophan. One-ml portion of the culture was inoculated in 50 ml of M9 minumum medium (0.6% $Na_2HPO_4$, 0.3% $KH_2PO_4$, 0.05% NaCl, 0.1% $NH_4Cl$, 2 mM $MgSO_4$, 0.2% glucose and 0.1 mM $CaCl_2$) containing 50 µg/ml of ampicillin and 1% Casamino acid and incubated at 37° C. with shaking. The cells were harvested when the absorbance (O.D.) at 550 mµ reach 1.0 and suspended in 5 ml of a solution of 15% sucrose, 50 mM tris-HCl (pH 8.0) and 50 mM EDTA (pH 8.0). A 500 µl of 10 mg/ml of lysozyme (as dissolved in 10 mM tris-HCl (pH 8.0)) was added to the suspension, and 5 ml of a solution of 0.3% Triton X100, 187.5 mM EDTA (pH 8.0) and 150 mM tris-HCl (pH 8.0) was further added. The mixture was allowed to stand at room temperature for 15 minutes, then thoroughly stirred and centrifuged to obtain a supernatant of cell extract.

The supernatant was checked for GIF activity with the result given in Table 6. The activity determined was $2 \times 10^6$ units/ml culture.

TABLE 6

| Specimen | GIF activity (units/ml culture) |
|---|---|
| Control 1 (assay medium) | Not detected |
| Control 2 (E. coli HB101 extract) | Not detected |
| E. coli HB101/ptrpGIF extract | $2 \times 10^6$ |

Ion-exchange chromatograph (CM-HPLC)

The cell culture supernatant prepared as above was dialyzed with 50 mM sodium acetate buffer (pH 5.5), and the dialyzate was subjected to ion-exchange chromatography (CM-HPLC) using Gilson high permeation liquid chromatography system (Gilson) under the following conditions.

Column: IEX-535CM (6.0×150 mm, Toyo Soda Co., Ltd.)
Eluent A: 50 mM sodium acetate (pH 5.5)
Eluent B: 50 mM sodium acetate (pH 5.5) containing 0.5M NaCl
Flow rate: 0.5 ml/min.

| Fraction volume: | Retention time: |
| --- | --- |
| 0–60 min | 2 ml/4 min/tube |
| 60–120 min | 0.5 ml/min/tube |
| 120–180 min | 2 ml/4 min/tube |

Concentration gradient:

| Time (min) | % B |
| --- | --- |
| 0 | 0 |
| 40 | 0 |
| 120 | 20 |
| 140 | 100 |
| 165 | 100 |
| 170 | 0 |

Reverse-phase high-performance liquid chromatography

The CM-HPLC procedure results in a GIF active fraction with a retention time of 90 to 91 minutes.

The active fraction was then subjected to reverse-phase high-performance liquid chromatography under the following conditions.

Column: C$_4$ Highpore reverse-phase column (RP304, Bio-Rad, 250 mm×4.6 mm (diam.))

| Eluents | A liquid = 0.1% TFA |
| --- | --- |
|  | B liquid = acetonitrile-1% TFA (9:1) |
| Flow rate | 1 ml/min. |
| Chart speed | Retention time: |
|  | 0–50 min . . . 5 min/cm |
|  | 50–80 min . . . 2 min/cm |

Concentration gradient:

| Time (min) | % B |
| --- | --- |
| 0 | 0 |
| 5 | 0 |
| 15 | 20 |
| 75 | 45 |
| 80 | 100 |
| 85 | 100 |
| 90 | 0 |

Fraction volume: 2 ml/2 min/tube

A fraction with a retention time of 63.9 to 65.3 minutes gave r-GIF exhibiting a single protein absorbance peak matching that of native GIF.

The specific activity was $2.7 \times 10^7$ units/mg protein.

The results (FIG. 3) of the reverse-phase high-performance chromatography of the natural type GIF conducted in Example 1, (I) shows that the GIF activity of the natural type GIF does not agree with LAF activity, which, however, is observed very broadly in the GIF active fraction, so that r-GIF obtained above was also checked for LAF activity. Consequently, r-GIF was found to have LAF activity.

SDS polyacrylamide gel electrophoresis (SDS-PAGE)

The molecular size of r-GIF obtained by the procedure (II) was determined with SDS-PAGE by the method of Laemmli, U. K. (Nature, 277, 680 (1970)) under the following conditions.

Specimen: The GIF-active fraction obtained by the CM-HPLC procedure was completely dried, then dissolved in Laemmli sample buffer (not containing 2-mercapto ethanol (2ME$^-$) or containing 2-mercapto ethanol in an amount of 1/20 the volume of the buffer (2ME$^+$)) and treated at 100° C. for 4 minutes.

Gel: 15% Polyacrylamide gel 1.15 mm in thickness
Apparatus: Protean, product of Bio-Rad
Electrophoresis: 40 mA constant current for 2 hours The gel resulting from the electrophoresis was stained with Silver Stain Kit (Bio-Rad) with the results shown in FIG. 17 (in the caseof 2ME$^+$) and FIG. 18 (for 2ME$^-$).

With reference to these drawings, lane (1) resulted from the following molecular weight markers, lane (2) to (6) from the r-GIF specimen, and lane (7) from natural type GIF specimen. The amounts of r-GIF specimen used were 11.7 ng for lane (2), 23.3 ng for lane (3), 46.6 ng for lane (4), 70 ng for lane (5) and 117 ng for lane (6).

Molecular weight markers for lane (1)
94K: Phosphorylase b
67K: Albumin
43K: Ovalbumin
30K: Carbonic anhydrase
20.1K: Trypsin inhibitor
14.4K: α-Lactoalubumin The results indicate that r-GIF is migrated as a single band at the position of about 17K in the case of 2ME$^+$ or of about 17.5K in the case of 2ME$^{-1}$.

Isoelectroforcussing (IEF)

r-GIF was was subjected to IEF using PAG plate (LKB) 3.5 to 9.5 in pH range, and Model 1415 (Bio-Rad) under the following conditions.

Specimen: The transformant obtained by the procedure of preparation of r-GIF (II) was broken down by osmotic pressure shock, and the resulting supernatant (10 mM tris-HCl, pH 8.0) was diluted 100-fold with distilled water. Ten μl of the dilution was used.

| Electrode solutions | Anode solution = 1M H$_3$PO$_4$ |
| --- | --- |
|  | Cathode solution = 1M NaOH |
| Electrophoresis | With constant power of 1W/cm gel width with cooling (10° C.) for 90 minutes |

Staining: With silver stain Kit
The gel resulting from the electrophoresis was sliced at a spacing of 5 mm or 2.5 mm, subjected to extraction with use of 1 ml of 10% FCS-added RPMI 1640 with shaking (for two days) and then checked for GIF activity. The isoelectric point was calculated from the pH measurement after the electrophoresis.

r-GIF had an isoelectric point (PI) of about 6.5 to about 6.9 and appeared as a single band at this position.

Amino acid composition r-GIF (30 μl) obtained by the reverse-phase high-performance liquid chromatographic procedure (II) was carefully placed into the bottom of a thick-walled hard test tube made of Pyrex glass and 12 mm×120 mm, and was dried in a vacuum in a desiccator containing sodium hydroxide pellets. A 50 μl quantity of 4N methane-sulfonic acid (containing 0.2% 3-(2-aminoethyl)indole and produced by Pierce) was added to the dry specimen within the tube. The interior of the tube was deaerated at 0.1 to 0.2 mm Hg for 1 minute and then sealed off. The specimen was hydrolyzed in a heater at 118° C. over a period of 24 hours. After opening the tube, the mixture was neutralized with 46 μl of 4N sodium hydroxide and diluted to an amount of 450 μl with citric acid buffer.

A 250 μl quantity of the specimen solution was used for amino acid analysis by an amino acid analyzer (Model HITACHI 835, product of Hitachi Ltd.). The amino acids separated were detected by the o-phthalaldehyde method and quantitatively determined with reference to calibration curves prepared with use of authentic amino acids.

Table 7 shows the results in terms of the mole ratio of component amino acids based on Phe (9 moles). Under the above analysis conditions, Pro and Cys are not determinable. For Ser, Thr, and Met, the percent recovery as achieved under the above conditions is given in parentheses.

TABLE 7

| Amino acid | Mole ratio |
| --- | --- |
| Asp and/or Asn | 17.1 |
| Ser | 10.9 (80%) |
| Thr | 5.4 (90%) |
| Glu and/or Gln | 23.8 |
| Gly | 8.3 |
| Ala | 5.0 |
| Val | 10.8 |
| Met | 5.5 (90%) |
| Ile | 4.9 |
| Leu | 15.1 |
| Tyr | 3.9 |
| Phe | (9) |
| Lys | 14.9 |
| His | 0.9 |
| Trp | 0.8 |
| Arg | 3.0 |

Amino acid sequence of r-GIF

A 150 μl quantity of r-GIF obtained by the reverse-phase high-performance chromatographic procedure (II) was analyzed by a protein sequencer (Applied Biosystems Inc.). Each resulting PTH-amino acid was suitably diluted with 100 to 50 μl of 33% aqueous acetonitrile solution, and 5-μl portion of the dilution was injected into a chromatographic column by an autosampler, Waters 710B. For the chromatographic system, two pumps, Beckman Model 112, were operated by a controller, Model 421. The column used, measuring 2 mm×250 mm and packed with Ultrasphere ODS-5 μm, was maintained at 55° C. by a column heater. The flow rate was 0.3 ml/min. A mixture of 20 mM sodium acetate and acetonitrile was used for gradient elution. Absorbance was monitored at 269 nm. Analysis was conducted for 45 minutes.

The results of 20 cycles of analysis revealed that r-GIF obtained by the procedure (II) had the following sequence of 20 amino acids at the N terminal.

Ala—Pro—Val—Arg—Ser—Leu—Asn—Cys—Thr—Leu—
Arg—Asp—Ser—Gln—Gln—Lys—Ser—Leu—Val—Met—

Arg was separately identified using a slightly modified HPLC system. Ser was identified by way of a by-product and was further identified at 322 nm. Cycle 8 showed no significant peak. It was speculated that the amino acid concerned was Cys.

The results given above indicate that r-GIF obtained by the procedure (II) agree with polypeptide I. The molecular weight of r-GIF calculated from the amino acid composition is 17376.59.

Antitumor activity in vivo r-GIF obtained in Example 2, (II) was tested in vivo for antitumor activity as described below.

1. One million viable A375 cells were inoculated s.c. in a BALB/c nude mouse on day 0. r-GIF was administered i.t. at a daily dose of 100000 units/body from days 10 to 15. Six mice were used for one group.

PBS only was similarly given to a control group.

The results are shown in FIG. 19 in which line (1) represents the control group, and line (2) represents the group given r-GIF.

2. A BALB/c mouse was intracutaneously inoculated with 200000 viable Meth A cells on day 0. r-GIF was administered i.t. at a daily dose of 100000 units/body on days 7 and 8. Seven mice were used for one group. PBS only was similarly given to a control group. FIG. 20 shows the results in which line (1) represents the control group and line (2) represents the group given r-GIF. Five in the test group exhibited regression of the tumor.

EXAMPLE 3

The desired r-GIF, such as polypeptide II, III or IV, can be prepared using plasmid pGIF-α obtained in Example 1, (II), (3–5) and following the same procedure as Example 2.

Peptide IV, for example, can be prepared by the following procedure.

Two DNA fragments are isolated from plasmid pGIF-α. One is HgiAI-NcoI DNA fragment (about 0.1 kbp) and the other is NcoI-StuI DNA fragment (about 0.8 kbp). The synthetic oligonucleotide having four amino acids codons of the amino terminal region of the polypeptide IV is ligated with HgiAI-NcoI DNA fragment to link with trp promoter. The DNA fragment thus obtained and NcoI-StuI DNA fragment are linked sequentially with the vector pTM1 the downstream of the trp promoter. This constituted a plasmid expresses polypeptide IV under the control of trp promoter in *E. coli*. The same procedure as in Example 2 is repeated with the use of the plasmid obtained above instead of the plasmid ptrpGIF-α to give polypeptide IV.

EXAMPLE 4 ptrpGIF-α was used for preparing GIF ($^{71}$Ser-r-GIF) having the amino acid sequence of polypeptide I wherein the 71st amino acid, Cys, from the N terminal was replaced by Ser, according to the site-specific mutagenesis method (Pro. Nat. Acad. Sci., 81, 5662–5666 (1984); Science, 224, 1431 1984)).

M13 mp 11 phage vector was used as a single-strand DNA template. EcoRI/BamHI DNA fragment was isolated from plasmid ptrpGIF-α and cloned in M13 mp 11 phage at restriction enzyme EcoRI and BamHi sites to obtain single-strand (ss) DNA (M13-GIF-α), which was then used as a mutagenesis template. Synthetic oligonucleotide [CTGTCCTCAGTGTTG (primer)] was phosphorylated with T4 polynucleotide kinase and hybridized with as M13-GIF-α DNA. The hybrid was annealed, thereafter treated with DNA polymerase I, (Klenow fragment) and T4 DNA ligase individually and incubated at 15° C. for 18 hours.

The DNA obtained was introduced into JM105 competent cell for transformation. The resulting phage plaque (50 colonies) was inoculated onto an agar plate and incubated at 37° C. for 18 hours. A filter containing the culture was treated with an alkali in the usual manner for denaturation, dried and then baked at 80° C. for 2 hours. The DNA was prehybridized and then hybridized at room temperature for 1 hour with $^{32}$P probe prepared by labeling the primer with $^{32}$P-r-ATP. The filter resulting from the hybridization was washed with 6X SSC buffer at room temperature for 10 minutes and further at 37° C. for 10 minutes, dried and thereafter subjected to autoradiography at −70° C. for 18 hours.

M13-GIF-71s was selected as a typical clone from among five mutant clones, infected with JM105 and incubated to prepare ssDNA and RF DNA.

M13 dideoxynucleotide sequencing was performed for ssDNA to confirm mutation of the contemplated gene.

Newly produced restriction enzyme DdeI site was also identified in RF DNA.

EcoRI/BamHI fragment was prepared from RF DNA produced in JM105, introduced into expression plasmid as in Example 2, (II) to obtain the desired $^{71}$Ser-r-GIF expression plasmid ptrpGIF-α-71S.

A cell extract supernatant was prepared with use of the plasmid in the same manner as in Example 2, (II) and checked for α-GIF activity. Table 8 shows the result.

TABLE 8

| Specimen | GIF activity (units/ml culture) |
|---|---|
| Control (E. coli HB101/ptrpGIF-α) | 473.8 × 10$^3$ |
| E. coli HB101/ptrpGIF-α-71S extract | 434.6 × 10$^3$ |

We claim:

1. A process for preparing an antitumor active substance GIF comprising the steps of causing an antitumor substance inducing substance to act on an immunologically competent cell derived from a human and collecting the GIF substance by sequential chromatography comprising gel-filtration chromatography, reverse-phase chromatography and chromatofocusing or ion-exchange chromatography, and the GIF substance is substantially a homogeneous protein, contains as its component protein, polypeptide A, having the following primary structure, and has a molecular weight of 18,000 and an isoelectric point of 6.88 to 7.02

Ala Pro Val Arg Ser Leu Asn Cys Thr Leu Arg Asp Ser
Gln Gln Lys Ser Leu Val Met Ser Gly Pro Tyr Glu Leu
Lys Ala Leu His Leu Gln Gly Gln Asp Met Glu Gln Gln
Val Val Phe Ser Met Ser Phe Val Gln Gly Glu Glu Ser
Asn Asp Lys Ile Pro Val Ala Leu Gly Leu Lys Glu Lys
Asn Leu Tyr Leu Ser Cys Val Leu Lys Asp Asp Lys Pro
Thr Leu Gln Leu Glu Ser Val Asp Pro Lys Asn Tyr Pro
Lys Lys Lys Met Glu Lys Arg Phe Val Phe Asn Lys Ile
Glu Ile Asn Asn Lys Leu Glu Phe Glu Ser Ala Gln Phe
Pro Asn Trp Tyr Ile Ser Thr Ser Gln Ala Glu Asn Met
Pro Val Phe Leu Gly Gly Thr Lys Gly Gly Gln Asp Ile
Thr Asp Phe Thr Met Gln Phe Val Ser Ser OH.

2. A process for preparing an antitumor active substance GIF, comprising the steps of incubating a recombinant microorganism having a replicon joined to a gene which codes for polypeptide A of the following structure Ala Pro Val Arg Ser Leu Asn Cys Thr Leu Arg Asp Ser Gln Gln
Lys Ser Leu Val Met Ser Gly Pro Tyr Glu Leu Lys Ala Leu His
Leu Gln Gly Gln Asp Met Glu Gln Gln Val Val Phe Ser Met Ser
Phe Val Gln Gly Glu Glu Ser Asn Asp Lys Ile Pro Val Ala Leu
Gly Leu Lys Glu Lys Asn Leu Tyr Leu Ser Ser Val Leu Lys Asp
Asp Lys Pro Thr Leu Gln Leu Glu Ser Val Asp Pro Lys Asn Tyr
Pro Lys Lys Lys Met Glu Lys Arg Phe Val Phe Asn Lys Ile Glu
Ile Asn Asn Lys Leu Glu Phe Glu Ser Ala Gln Phe Pro Asn Trp
Tyr Ile Ser Thr Ser Gln Ala Glu Asn Met Pro Val Phe Leu Gly
Gly Thr Lys Gly Gly Gln Asp Ile Thr Asp Phe Thr Met Gln Phe
Val Ser Ser OH and collecting the GIF by sequential chromatography comprising reverse-phase chromatography and chromatofocusing or ion-exchange chromatography, and the GIF is substantially a homogenous protein.

* * * * *

UNITED STATES PATENT AND TRADEMARK OFFICE
CERTIFICATE OF CORRECTION

PATENT NO. : 4,898,818
DATED : February 6, 1990
INVENTOR(S) : NAKAI, SATORU ET AL It is certified that error appears in the above-identified patent and that said Letters Patent is hereby corrected as shown below:

Title page item [30] Foreign Application Priority Data

Dec. 21, 1984 [JP] Japan.............................59-271207
        Jun. 24, 1985 [JP] Japan.............................60-138280
        Jun. 24, 1985 [JP] Japan.............................60-138281
        Oct.  3, 1985 [JP] Japan.............................60-220882
        <u>Dec. 16, 1985 [JP] Japan.............................60-283238</u>

Signed and Sealed this

Thirtieth Day of January, 2001

Attest:

Q. TODD DICKINSON

*Attesting Officer*      *Director of Patents and Trademarks*